(12) United States Patent
Lee et al.

(10) Patent No.: US 11,524,079 B2
(45) Date of Patent: *Dec. 13, 2022

(54) HYALURONAN CONJUGATES AND USES THEREOF

(71) Applicant: Aihol Corporation, Artesia, CA (US)

(72) Inventors: Szu-Yuan Lee, Taipei (TW); Ping-Shan Lai, Taipei (TW); Chih-An Lin, Taipei (TW)

(73) Assignee: AIHOL CORPORATION, Buena Park, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/891,020

(22) Filed: Jun. 2, 2020

(65) Prior Publication Data

US 2020/0376132 A1 Dec. 3, 2020

Related U.S. Application Data

(60) Provisional application No. 62/856,714, filed on Jun. 3, 2019.

(51) Int. Cl.
| | |
|---|---|
| *A61K 47/61* | (2017.01) |
| *A61K 31/566* | (2006.01) |
| *A61K 31/565* | (2006.01) |
| *A61P 25/28* | (2006.01) |
| *A61K 31/573* | (2006.01) |
| *A61K 47/54* | (2017.01) |
| *A61K 31/568* | (2006.01) |

(52) U.S. Cl.
CPC ............ *A61K 47/61* (2017.08); *A61K 31/565* (2013.01); *A61K 31/566* (2013.01); *A61K 31/568* (2013.01); *A61K 31/573* (2013.01); *A61K 47/542* (2017.08); *A61P 25/28* (2018.01)

(58) Field of Classification Search
CPC ..... A61K 47/61; A61K 47/542; A61K 31/565
See application file for complete search history.

(56) References Cited

U.S. PATENT DOCUMENTS

| | | | |
|---|---|---|---|
| 2009/0054537 | A1 | 2/2009 | Brown |
| 2010/0144035 | A1 | 6/2010 | Oh et al. |
| 2012/0294945 | A1 | 11/2012 | Hahn et al. |
| 2013/0116411 | A1 | 5/2013 | Pollock et al. |
| 2015/0065446 | A1 | 3/2015 | Lin |
| 2015/0231268 | A1* | 8/2015 | Nakai ............ A61K 47/61 |
| | | | 536/53 |
| 2019/0015518 | A1 | 1/2019 | Forrest et al. |
| 2019/0328891 | A1 | 10/2019 | Karel et al. |

FOREIGN PATENT DOCUMENTS

| | | |
|---|---|---|
| KR | 20170010651 A | 2/2017 |
| WO | 2011/148116 A2 | 12/2011 |

OTHER PUBLICATIONS

Wang; (Journal of Alzheimers disease; 2017, 57(4), 1041-1048) .*
Kavirajan et al. (Lancet Neurol 2007, 6, 782-92) Vattakatuchery et al., World Journal of Psychiatry; 2013, 3(.*
Vattakatuchery et al., World Journal of Psychiatry; 2013, 3(3), 62-64.*

* cited by examiner

*Primary Examiner* — Pancham Bakshi
(74) *Attorney, Agent, or Firm* — Patenttm.US

(57) ABSTRACT

Disclosed herein is a hyaluronan conjugate, which includes a hyaluronic acid (HA), a sex hormone, and a linker for coupling one of the disaccharide units of the HA and the sex hormone. Also disclosed herein are the uses of the hyaluronan conjugate in treating or preventing neurodegenerative diseases.

7 Claims, 13 Drawing Sheets
(1 of 13 Drawing Sheet(s) Filed in Color)

HYALURONAN CONJUGATES AND USES THEREOF

BACKGROUND OF THE INVENTION

1. Field of the Invention

The present disclosure in general relates to hyaluronic acid (HA)-sex hormone conjugates, and their uses in treating neurodegenerative diseases.

2. Description of Related Art

Neurodegenerative diseases of the central nervous system (CNS) are characterized by the progressive loss of structure and function of neurons, including the death of neurons, which is mainly manifested by dementia or movement with difficulty (e.g., resting tremor, stiffness, or lumbering). Among the neurodegenerative diseases, Alzheimer's disease (AD), Parkinson's disease (PD), amyotrophic lateral sclerosis (ALS), Multiple Sclerosis (MS), and Huntington's disease (HD) are very common in the neurology clinics. Neurodegenerative diseases are often associated with middle to old-age populations, and are quite devastating for the patients and their families. Such diseases adversely impact the patients' life quality, while at the same time pose a heavy burden to the medical system. However, with the advent of an aging society, the prevalence rate of neurodegenerative diseases is inevitably growing up.

To date, the treatments currently available for neurodegenerative diseases are only for mitigating the symptoms or for deferring the progression of the disease. For example, drugs like donepezil, galantamine, and rivastigmine are used to mitigate the cognitive, functional, and behavioral symptoms by delaying the catabolism of acetylcholine released into the synaptic cleft, so as to improve the nerve conduction activities. Also, drugs like levodopa, elldopa, and amantadine are used to defer the progression of the disease and increase the survival rate of the patients as well. Nevertheless, these drugs each has its own limitation and some even have serious side effects, and hence, the life quality of the patients remains disappointing.

In view of the foregoing, there exists in the related art a need for an effective treatment for neurodegenerative diseases.

SUMMARY

The following presents a simplified summary of the disclosure in order to provide a basic understanding to the reader. This summary is not an extensive overview of the disclosure and it does not identify key/critical elements of the present invention or delineate the scope of the present invention. Its sole purpose is to present some concepts disclosed herein in a simplified form as a prelude to the more detailed description that is presented later.

In one aspect, the present disclosure is directed to a hyaluronan conjugate.

According to various embodiment of the present disclosure, the hyaluronan conjugate comprises a hyaluronic acid (HA) or a derivative or salt thereof, a sex hormone and a linker that covalently coupling the sex hormone to one of the disaccharide units of the HA or HA derivative or HA salt.

In some embodiments, the sex hormone can be estrone, estradiol, estriol, testosterone, or 11-deoxycorticosterone.

According to optional embodiments of the present disclosure, the linker of the present hyaluronan conjugate is any of, one or more amino acids, lipid, dihydrazide-$C_2$-$C_{20}$ dicarboxylic acid, and $C_2$-$C_{20}$ dicarboxylic acids.

In one embodiment, the linker is an amino acid, such as β-alanine (β-ALA). In another embodiment, the linker is a dihydrazide-$C_2$-$C_{20}$ dicarboxylic acid, e.g., an adipic acid dihydrazide (ADH)-succinate. In yet another embodiment, the linker is a $C_2$-$C_{20}$ dicarboxylic acid; for example, a succinic acid.

According to other embodiments of the present disclosure, the HA of the present hyaluronan conjugate has a degree of substitution of 0.1% to 60%.

According to certain embodiments of the present disclosure, the HA of the present hyaluronan conjugate has a weight-average molecular weight (Mw) of about 5-500 kilodaltons (kDa). According to various embodiments of the present disclosure, the linker is coupled to the hydroxyl group (—OH) of the sex hormone.

Another aspect of the present disclosure is directed to a method for treating neurodegenerative diseases in a subject in need thereof.

According to some embodiments of the present disclosure, the method comprises the step of administering to the subject an effective amount of the present hyaluronan conjugate.

According to some embodiments of the present disclosure, the present hyaluronan conjugate is administered to the subject via oral, nasal, intracranial, intraspinal, intrathecal, intramedullary, intracerebral, intracerebroventricular, intravenous, intraarterial, intracardial, intracutaneous, subcutaneous, transdermal, intraperitoneal, or intramuscular administration.

According to some embodiments of the present disclosure, the neurodegenerative disease that can be treated using the present hyaluronan conjugate is Alzheimer's disease (AD), Parkinson's disease (PD), amyotrophic lateral sclerosis (ALS), multiple sclerosis (MS), Huntington's disease (HD), frontotemporal dementia, epilepsy, neuropathic pain, or ataxia.

According to some embodiments of the present disclosure, the subject treatable by the present hyaluronan conjugate is a mammal, preferably a human.

Subject matters that are also included in other aspects of the present disclosure include the use of a hyaluronic conjugate in the manufacture of a medicament for use in the treatment of neurodegenerative diseases, as well as a hyaluronic conjugate or a pharmaceutical composition comprising the same for use in the treatment of neurodegenerative diseases.

Many of the attendant features and advantages of the present disclosure will becomes better understood with reference to the following detailed description considered in connection with the accompanying drawings.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

These and other features, aspects and advantages of the present invention will become better understood with reference to the following description, appended claims and the accompanying drawings, where:

DESCRIPTION

Figure 1:
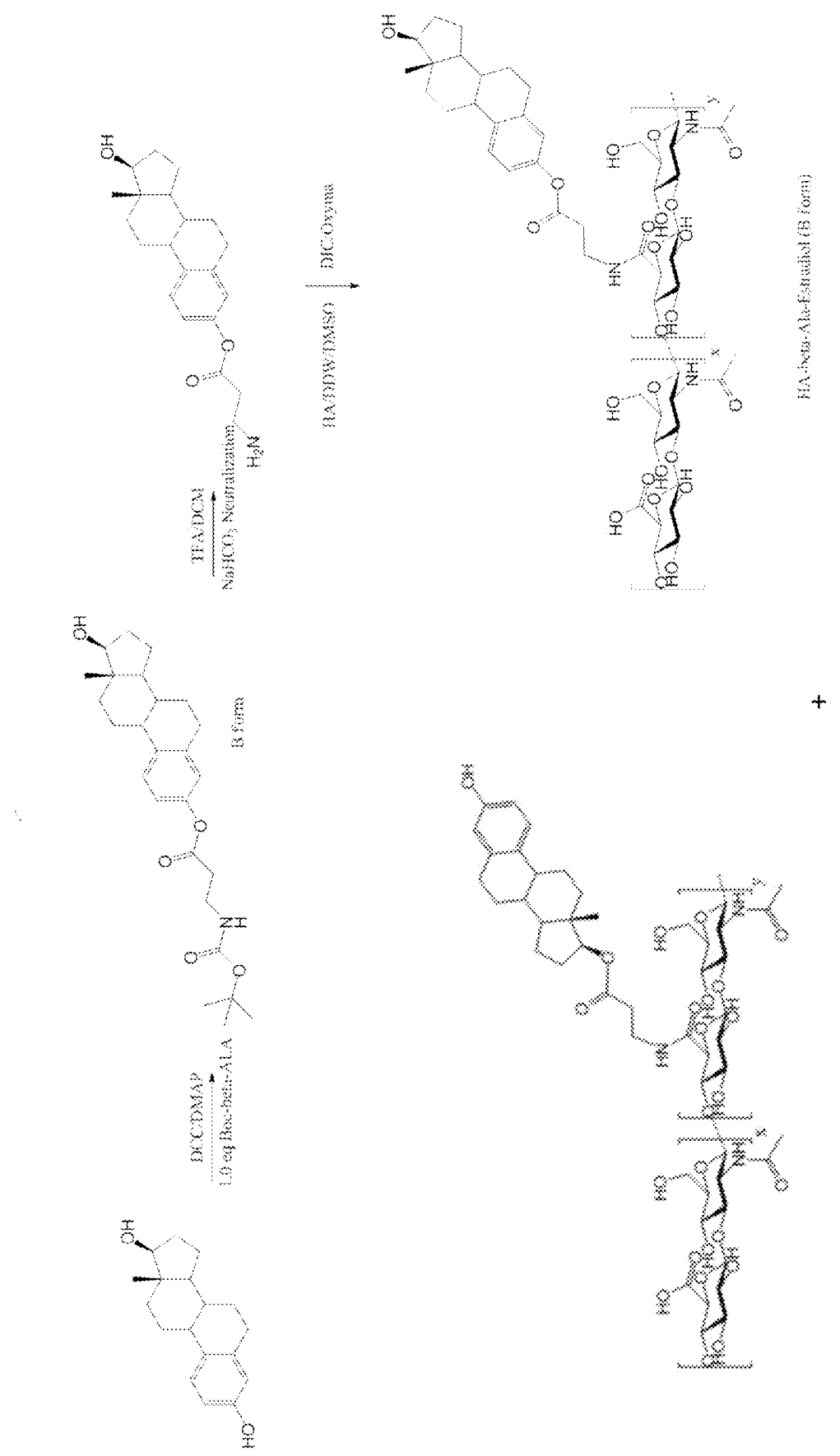
FIG. 1 is scheme for synthesizing the HA-βALA-C3/C17 estradiol (HA-E2) hyaluronan conjugate, according to one working example of the present disclosure.

The detailed description provided below in connection with the appended drawings is intended as a description of the present examples and is not intended to represent the only forms in which the present example may be constructed or utilized. The description sets forth the functions of the example and the sequence of steps for constructing and operating the example. However, the same or equivalent functions and sequences may be accomplished by different examples.

For convenience, certain terms employed in the specification, examples and appended claims are collected here. Unless otherwise defined herein, scientific and technical terminologies employed in the present disclosure shall have the meanings that are commonly understood and used by one of ordinary skill in the art.

Unless otherwise required by context, it will be understood that singular terms shall include plural forms of the same and plural terms shall include the singular. Also, as used herein and in the claims, the terms "at least one" and "one or more" have the same meaning and include one, two, three, or more. Furthermore, the phrases "at least one of A, B, and C", "at least one of A, B, or C" and "at least one of A, B and/or C," as use throughout this specification and the appended claims, are intended to cover A alone, B alone, C alone, A and B together, B and C together, A and C together, as well as A, B, and C together.

Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in the respective testing measurements. Also, as used herein, the term "about" generally means within 10%, 5%, 1%, or 0.5% of a given value or range. Alternatively, the term "about" means within an acceptable standard error of the mean when considered by one of ordinary skill in the art. Other than in the operating/working examples, or unless otherwise expressly specified, all of the numerical ranges, amounts, values and percentages such as those for quantities of materials, durations of times, temperatures, operating conditions, ratios of amounts, and the likes thereof disclosed herein should be understood as modified in all instances by the term "about". Accordingly, unless indicated to the contrary, the numerical parameters set forth in the present disclosure and attached claims are approximations that can vary as desired. At the very least, each numerical parameter should at least be construed in light of the number of reported significant digits and by applying ordinary rounding techniques. Ranges can be expressed herein as from one endpoint to another endpoint or between two endpoints. All ranges disclosed herein are inclusive of the endpoints, unless specified otherwise.

The terms "treatment" and "treating" as used herein may refer to a preventative (e.g., prophylactic), curative or palliative measure. In particular, the term "treating" as used herein refers to the application or administration of the present hyaluronan conjugate or a pharmaceutical composition comprising the same to a subject, who has a medical condition (e.g., a neurodegenerative disease), a symptom associated with the medical condition, a disease or disorder secondary to the medical condition, or a predisposition toward the medical condition, with the purpose to partially or completely alleviate, ameliorate, relieve, delay onset of, inhibit progression of, reduce severity of, and/or reduce incidence of one or more symptoms or features of said particular disease, disorder, and/or condition. Treatment may be administered to a subject who does not exhibit signs of a disease, disorder, and/or condition, and/or to a subject who exhibits only early signs of a disease, disorder and/or condition, for the purpose of decreasing the risk of developing pathology associated with the disease, disorder and/or condition.

The terms "subject" and "patient" are used interchangeably herein and are intended to mean an animal including the human species that is treatable by the hyaluronan conjugate described herein, pharmaceutical compositions comprising the same, and/or methods of the present invention. Accordingly, the term "subject" or "patient" comprises any mammal, which may benefit from the present disclosure. The term "mammal" refers to all members of the class Mammalia, including humans, primates, domestic and farm animals, such as rabbit, pig, sheep, and cattle; as well as zoo, sports or pet animals; and rodents, such as mouse and rat. The term "non-human mammal" refers to all members of the class Mammalis except human. In one exemplary embodiment, the patient is a human. The term "subject" or "patient" intended to refer to both the male and female gender unless one gender is specifically indicated.

The term "effective amount" as used herein refers to the quantity of the present hyaluronan conjugate that is sufficient to yield a desired therapeutic response. An effective amount of an agent is not required to cure a disease or condition but will provide a treatment for a disease or condition such that the onset of the disease or condition is delayed, hindered or prevented, or the disease or condition symptoms are ameliorated. The effective amount may be divided into one, two, or more doses in a suitable form to be administered at one, two or more times throughout a designated time period. The specific effective or sufficient amount will vary with such factors as particular condition being treated, the physical condition of the patient (e.g., the patient's body mass, age, or gender), the type of mammal or animal being treated, the duration of the treatment, the nature of concurrent therapy (if any), and the specific formulations employed and the structure of the compounds or its derivatives. Effective amount may be expressed, for example, as the total mass of the hyaluronan conjugate or the equivalent mass of the sex hormone in the hyaluronan conjugate (e.g., in grams, milligrams or micrograms) or a ratio of mass of the hyaluronan conjugate or the equivalent mass of the sex hormone in the hyaluronan conjugate to body mass, e.g., as milligrams per kilogram (mg/kg).

The terms "application" and "administration" are used interchangeably herein to mean the application of a hyaluronan conjugate or a pharmaceutical composition of the present invention to a subject in need of a treatment thereof.

According to some examples of the present disclosure, the hyaluronan conjugate is administered twice weekly during the test period. As could be appreciated, the effective amount can be adjusted accordingly depending on the interval and duration of administration. In certain embodiments, when multiple doses are administered to a subject, the frequency of administering the multiple doses to the subject is three doses a day, two doses a day, one dose a day, one dose every other day, one dose every third day, one dose every fourth day, one dose every fifth day, one dose every sixth day, one dose every week, one dose every other week, one dose monthly or one dose every other month. In certain embodiments, the frequency of administering the multiple doses to the subject is one dose per day. In certain embodiments, the frequency of administering the multiple doses to the subject is two doses per day. In certain embodiments, when multiple doses are administered to a subject, the duration between the first dose and last dose of the multiple doses is one day, two days, four days, one week, two weeks, three weeks, one month, two months, three months, four months, six months, nine months, one year, two years, three years, four years, five years, seven years, ten years, fifteen years, twenty years, or the lifetime of the subject. In certain embodiments, the duration between the first dose and last dose of the multiple doses is three months, six months, or one year. In certain embodiments, the duration between the first dose and last dose of the multiple doses is the lifetime of the subject. In a specific embodiment, the frequency of administering the multiple doses to the subject is three doses per week.

Also, according to the examples provided hereinbelow, the hyaluronan conjugate is administered via i.v. injection; however, this is only an illustration as to how the present invention can be implemented, and the present disclosure is not limited thereto.

For example, the hyaluronan conjugate can be formulated, together with a pharmaceutically-acceptable excipient, into a pharmaceutical composition suitable for the desired mode of administration. Certain pharmaceutical compositions prepared in accordance with the presently disclosed and claimed inventive concept(s) are single unit dosage forms suitable for oral, parenteral (e.g., subcutaneous, intravenous, bolus injection, intramuscular, or intraarterial), intravitreal, or transdermal administration to a patient. Examples of dosage forms include, but are not limited to, tablets; caplets; capsules, such as soft elastic gelatin capsules; cachets; troches; lozenges; dispersions; suppositories; ointments; cataplasms (poultices); pastes; powders; dressings; creams; plasters; solutions; patches; aerosols (e.g., nasal sprays or inhalers); gels; liquid dosage forms suitable for oral administration to a patient, including suspensions (e.g., aqueous or non-aqueous liquid suspensions, oil-in-water emulsions, or a water-in-oil liquid emulsions), solutions, and elixirs; liquid dosage forms suitable for parenteral administration to a patient; and sterile solids (e.g., crystalline or amorphous solids) that can be reconstituted to provide liquid dosage forms suitable for parenteral administration to a patient. As could be appreciated, these pharmaceutical compositions are also within the scope of the present disclosure.

The phrase "pharmaceutically acceptable excipient" as used herein means a pharmaceutically acceptable material, composition or vehicle, such as a liquid or solid filler, diluent, carrier, solvent or encapsulating material, involved in carrying or transporting the subject agents from one organ, or portion of the body, to another organ, or portion of the body. Each excipient must be "acceptable" in the sense of being compatible with the other ingredients of the formulation. The pharmaceutical formulation contains a compound of the invention in combination with one or more pharmaceutically acceptable ingredients. The excipient can be in the form of a solid, semi-solid or liquid diluent, cream or a capsule. These pharmaceutical preparations are a further object of the invention. Usually, the amount of active compounds is between 0.1-95% by weight of the preparation, preferably between 0.2-20% by weight in preparations for parenteral use and preferably between 1 and 50% by weight in preparations for oral administration. For the clinical use of the methods of the present invention, the pharmaceutical composition of the invention is formulated into formulations suitable for the intended route of administration.

The term "degree of substitution (DS)" of the HA conjugate, as used herein, is the average ratio of substituent groups (i.e., the sex hormone) attached per disaccharide unit of the HA.

As used herein, the term "hyaluronic acid" (HA) (also called hyaluronate or hyaluronan) is an anionic, nonsulfated glycosaminoglycan composed of a repeating sequence of disaccharide units, specifically a D-glucuronic acid and a N-acetyl-D-glucosamine (−4GlcUAβ1-3GlcNAcβ1-). Its molecular weight can range from 379 Dalton (Da) (the single disaccharide unit) to over millions of daltons. HA is involved in cell motility and immune cell adhesion by interaction with the cell surface receptor for hyaluronan-mediated motility (RHAMM) and CD44. The term "HA derivative" refers to an HA having any modification on the hydroxyl, carboxyl, amide or acetylamino groups of one or more disaccharide units of the HA.

As used herein, the term "salt" refers to any and all salts, and encompasses pharmaceutically acceptable salts. The term "pharmaceutically acceptable salt" refers to those salts which are, within the scope of sound medical judgment, suitable for use in contact with the tissues of humans and lower animals without undue toxicity, irritation, allergic response, and the like, and are commensurate with a reasonable benefit/risk ratio. Pharmaceutically acceptable salts are well known in the art.

As used herein, the term "linker" means a chemical moiety (e.g., a chemical bond form between two functional groups) that connects two parts of a conjugate. In the present disclosure, the linker may be any chemical moiety present between the sex hormone and the HA. In some embodiments of the present disclosure, the linker may be digested chemically or enzymatically; alternatively, it may degrade spontaneously.

According to preferred embodiments of the present disclosure, the present hyaluronan conjugate is formulated into a "modified release (MR)" formulation, such as extended-release (ER), controlled-release (CR), sustained-release (SR), prolonged release (PR), long-acting release (LAR) and delayed-release (DR) drug products. As opposed to conventional dosage forms that often give prompt release of the drug substance thereby showing fluctuations in drug concentration in the body and necessitating multiple dosing to maintain the therapeutic level of the drug substance, in modified release dosage forms, release characteristics of time course and/or location of the drug substance are chosen to accomplish the desired therapeutic objectives not offered by conventional dosage forms. The terminologies with respect to the dosage forms shall have their ordinary meanings as recognized and used by persons having ordinary skill in the art. For example, the term "extended-release" is a dosage form that allows at least a twofold reduction in dosage frequency as compared to that drug presented as an immediate-release (conventional) dosage form. The term "controlled release" refers to dosage forms from which drug substance may be delivered over a prolonged period of time; in the case of injectable dosage forms, this period may vary from day to months. The term "sustained release" refers to the release of the drug substance at a predetermined rate leading to a constant plasma concentration for a period of time.

The present disclosure is based, at least in part, on an unexpected discovery that HA-sex hormone conjugates exhibit desirable therapeutic effect on treating various neurodegenerative diseases, while at the same time reduce the unwanted side effects caused by sex hormones acting on other organs, such as breast and heart.

Accordingly, the first aspect of the present disclosure is directed to a hyaluronan conjugate that comprises a hyaluronic acid (HA) or a derivative or a salt thereof, a sex hormone, and a linker for coupling the sex hormone to one of the disaccharide units of the HA or the HA derivative or HA salt.

For example, the sex hormone can be any of estrone (E1), estradiol (E2), estriol (E3), testosterone (T), and 11-deoxycorticosterone (11-DOC).

According to various embodiments, the linker may be one or more amino acid residues, a lipid, a dihydrazide-$C_2$-$C_{20}$ dicarboxylic acid, or a $C_2$-$C_{20}$ dicarboxylic acid. In present disclosure, the linker serves as an arm or a spacer for connecting the HA and the sex hormone. The linker engages, on one side, the HA via a hydroxyl, carboxyl, amide, or acetylamino group linkage, and, on the other side, the sex hormone via any possible covalent bond.

In some embodiments, the linker is a single amino acid residue, such as, alanine (Ala; preferably, β-alanine), arginine (Arg), asparagine (Asn), aspartic acid (Asp), cysteine (Cys), glutamic acid (Glu), glutamine (Gln), glycine (Gly), histidine (His), isoleucine (Ilu), leucine (Leu), lysine (Lys), methionine (Met), phenylalanine (Phe), proline (Pro), serine (Ser), threonine (Thr), tryptophan (Trp), tyrosine (Tyr), valine (Val), γ-abu (4-aminobutanoic acid), δ-aminovaleric acid (5-aminopentanoic acid), ε-aminocaproic acid (6-aminohexanoic acid), 7-aminoheptanoic acid, 8-aminooctanoic acid, and 11-aminoundecanoic acid. In some embodiments, the linker may be a short peptide having two to 100 amino acid residues. For example, the linker may be a flexible peptide having a sequence of $(G_nS)_m$, where n and m are independently a number between 1 to 4.

In some embodiments, a lipid linker is preferred. Such lipid linkers have a hydrophilic polar head group and a hydrophobic chain.

In some embodiments, the linker is a linear or branched, aliphatic, aromatic or araliphatic $C_2$-$C_{20}$ dicarboxylic acids, which may be a derivative of, for example, oxalic acid, malonic acid, succinic acid, glutaric acid, adipic acid, pimelic acid, suberic acid, azelaic acid, sebacic acid, dodecanedioic acid, brassylic acid, thapsic acid, diabolic acids, crocetin, maleic acid, fumaric acid, glutaconic acid, 2-decenedioic acid, traumatic acid, muconic acid, glutinic acid, citraconic acid, mesaconic acid, itaconic acid, tartronic acid, mesoxalic acid, malic acid, tartaric acid, oxaloacetic acid, aspartic acid, α-hydroxyglutaric acid, arabinaric acid, acetonedicarboxylic acid, α-ketoglutaric acid, glutamic acid, diaminopimelic acid, saccharic acid, phthalic acid, isophthalic acid, terephthalic acid, diphenic acid, and 2,6-naphthalenedicarboxylic acid.

A dihydrazide-$C_2$-$C_{20}$ dicarboxylic acid-based linker generally has two moieties, i.e., a dihydrazide and $C_2$-$C_{20}$ dicarboxylic acid, in which one carboxylate group of the $C_2$-$C_{20}$ dicarboxylic acid is covalently bonded with one hydrazide group of the dihydrazide. Examples for the dihydrazide moiety include, but are not limited to adipic acid dihydrazide (ADH), sebacic acid dihydrazide (SDH), valine dihydrazide (VDH), isophthalic dihydrazide (IDH), carbodihydrazide (CDH), icosanedioic acid dihydrazide (LDH), succinic dihydrazide, adipic dihydrazide, dihydrazide sulfoxide, oxalic dihydrazide, and pimelic acid dihydrazide. Illustrative examples described above in connection with the $C_2$-$C_{20}$ dicarboxylic acid linker are also suitable for use as the dicarboxylic acid moiety for dihydrazide-$C_2$-$C_{20}$ dicarboxylic acid-based linkers.

The present linker also encompasses an amino-C2-C20 dicarboxylic acid-based linker, which has two moieties, i.e., one or more amino acids and C2-C20 dicarboxylic acid. Illustrative examples described above in connection with the amino acid residues and the C2-C20 dicarboxylic acid linker are also suitable for use to form such as t amino-C2-C20 dicarboxylic acid-based linker. As an example, rather than a limitation, the amino-C2-C20 dicarboxylic acid-based linker can be an ALA-succinate linker.

According to some embodiments of the present disclosure, the HA of the present hyaluronan conjugate has a weight-average molecular weight (Mw) ranging from about 5 kDa to about 500 kDa, for example, about 5, 6, 7, 8, 9, 10, 15, 20, 25, 30, 35, 40, 45, 50, 55, 60, 65, 70, 75, 80, 85, 90, 95, 100, 110, 120, 130, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, 450, 460, 470, 480, 490, or 500 kDa.

According to some embodiments of the present disclosure, the HA of the present hyaluronan conjugate may be in an unsubstituted (i.e., the HA per se) or a substituted (i.e., the HA derivative) form, or may be a salt thereof. As described above, HA can be modified on its functional groups such as hydroxyl, carboxyl, amide or acetylamino groups. HA can be modified by esterification, grafting and/or hydrophobization on its functional groups (i.e., hydroxyl, carboxyl, amide or acetylamino groups) as described above through reaction with a series of chemical agents. Exemplary HA derivatives are ethylsulfonated HA, deacetylated HA, or hydrazide-modified HA. In one example of the present disclosure, the HA of the present hyaluronan conjugate is in an unsubstituted form. In another example of the present disclosure, the HA of the present hyaluronan conjugate is in a substituted form.

According to various embodiments of the present disclosure, the present hyaluronan conjugate has a degree of substitution with the sex hormone of 0.1 to 60%. For example, the DS may be 0.1, 0.2, 0.3, 0.4, 0.5, 0.6, 0.7, 0.8, 0.9, 1, 1.5, 2, 2.5, 3, 3.5, 4, 4.5, 5, 5.5, 6, 6.5, 7, 7.5, 8, 8.5, 9, 9.5, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, or 60%.

The conjugated disaccharide unit of some representative hyaluronic conjugates of the present invention are summarized in Table 1 below; however, the present invention is not limited thereto. As could be appreciated, the stereoisomers of the illustrative sex hormone shown in Table 1 are also envisaged by the present inventors.

TABLE 1

| No. | Chemical Structure | Sex Hormone | Linker |
|---|---|---|---|
| I | 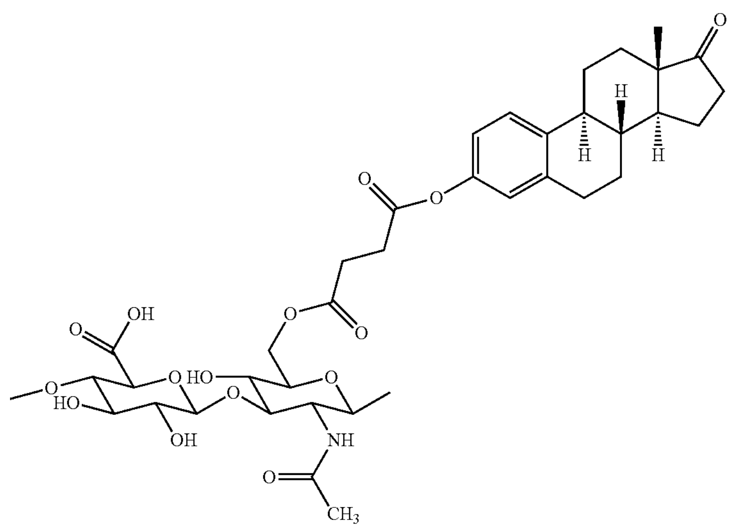 | E1 | Succinate |
| II | 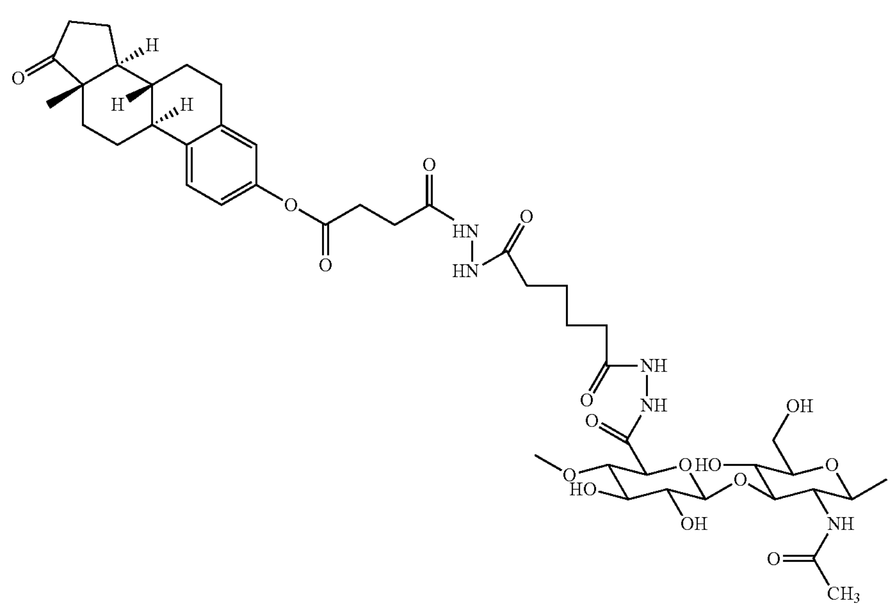 | E1 | ADH-Succinate |

TABLE 1-continued

| No. | Chemical Structure | Sex Hormone | Linker |
|---|---|---|---|
| III | 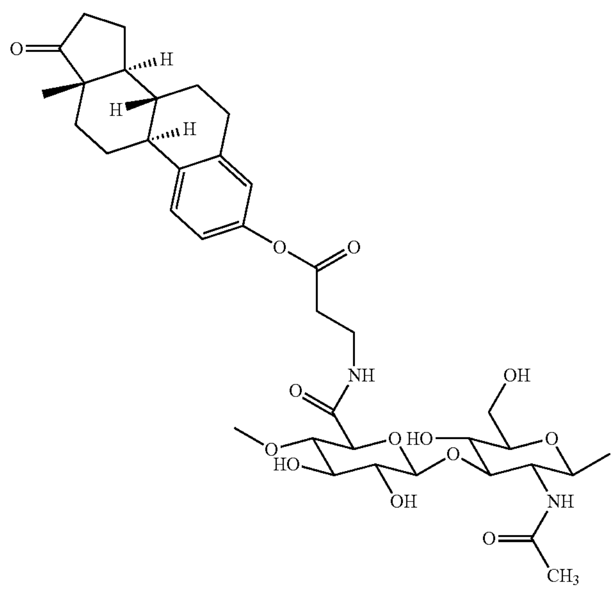 | E1 | β-Ala |
| IV | 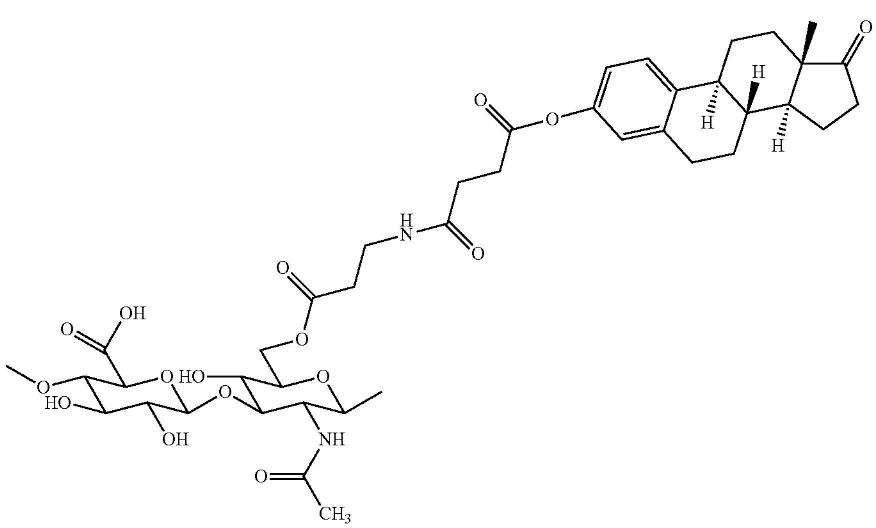 | E1 | β-Ala-succinate |

TABLE 1-continued

| No. | Chemical Structure | Sex Hormone | Linker |
|---|---|---|---|
| V | 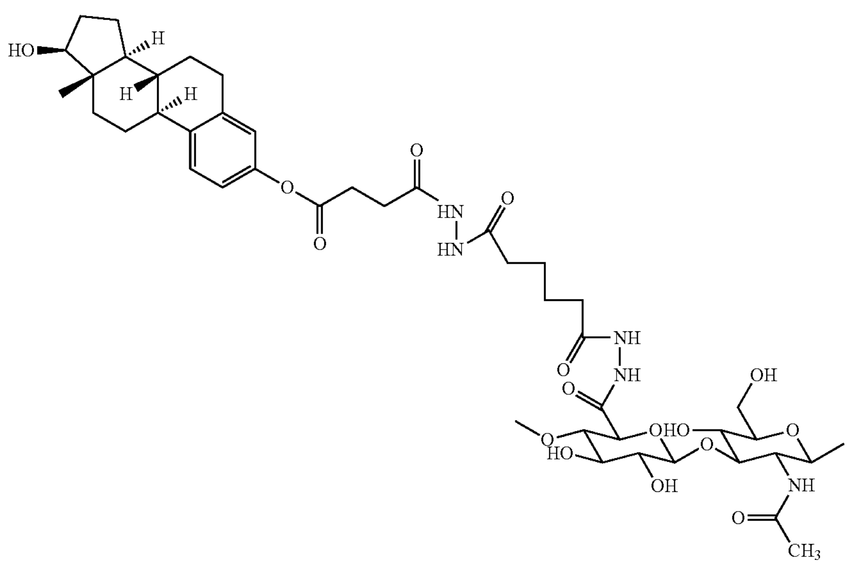 | E2 | ADH-succinate |
| VI | 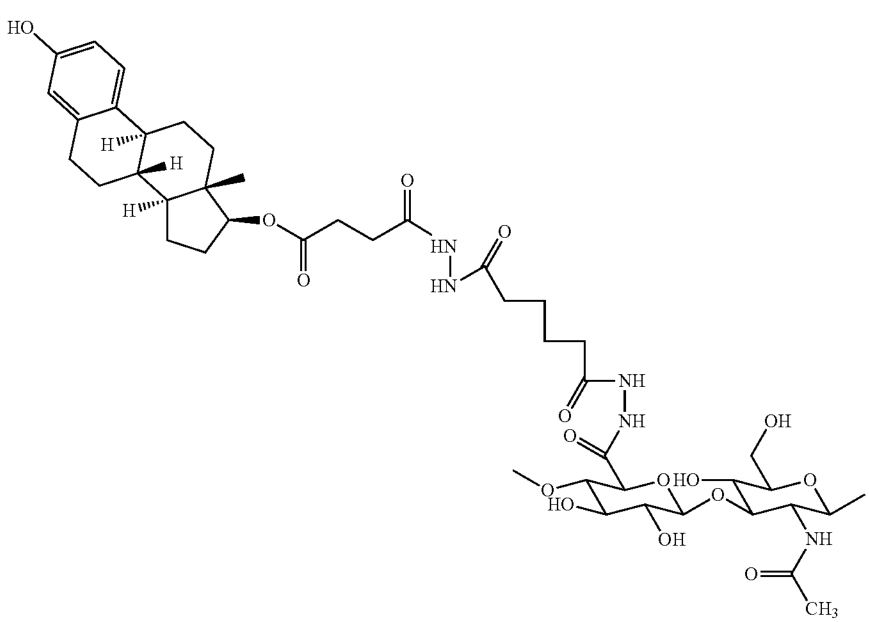 | E2 | ADH-succinate |

TABLE 1-continued

| No. | Chemical Structure | Sex Hormone | Linker |
|---|---|---|---|
| VII | 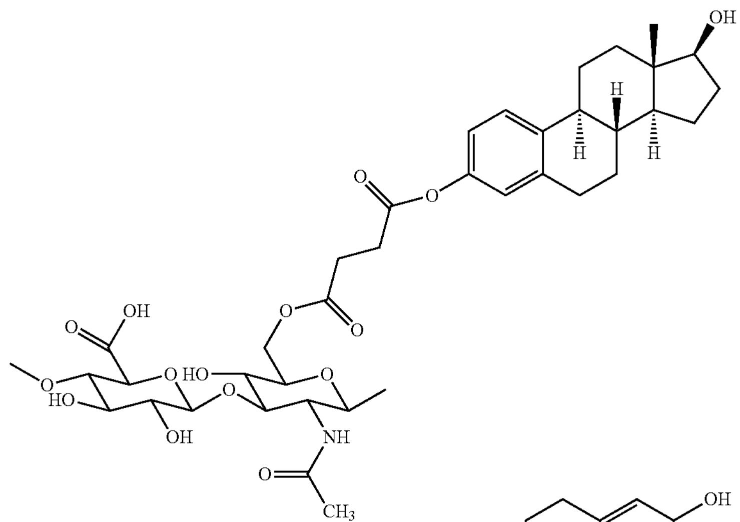 | E2 | Succinate |
| VIII | 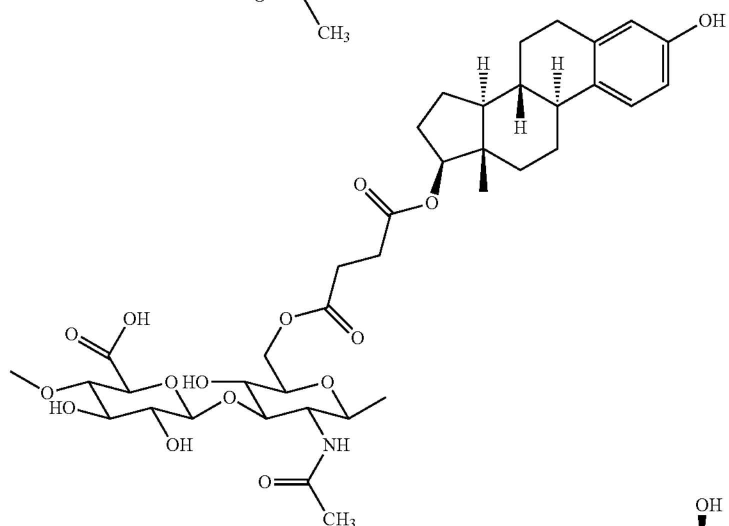 | E2 | Succinate |
| IX | 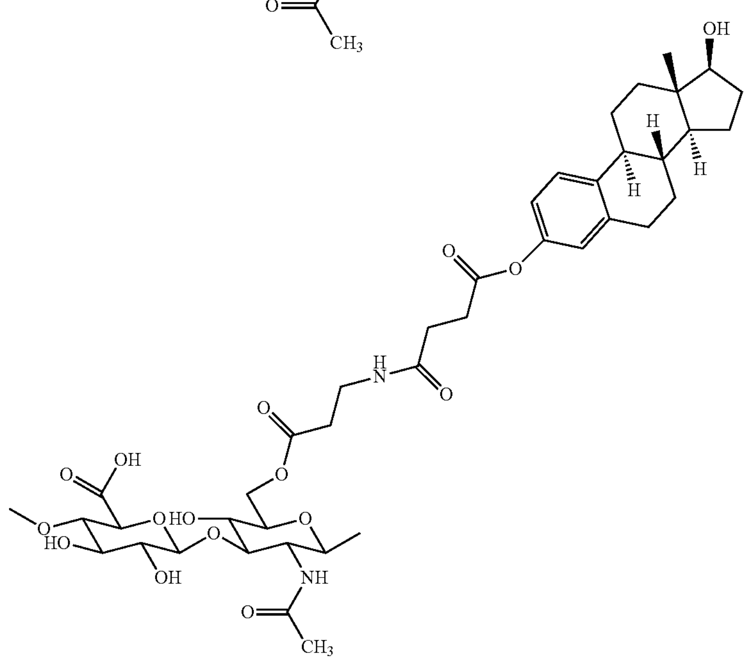 | E2 | β-Ala-succinate |

TABLE 1-continued
| No. | Chemical Structure | Sex Hormone | Linker |
|---|---|---|---|
| X | 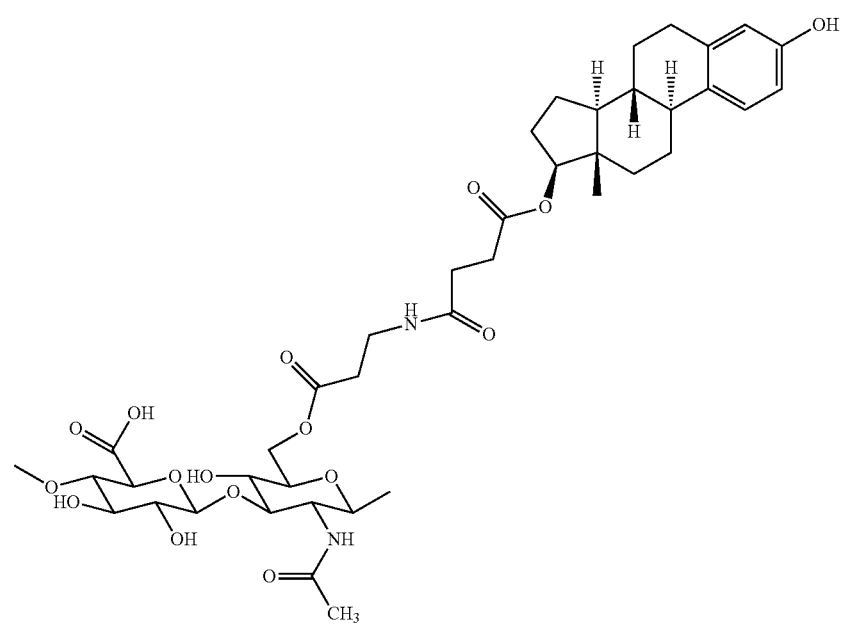 | E2 | β-Ala-succinate |
| XI | 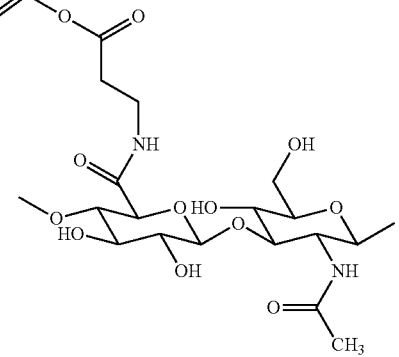 | E2 | β-Ala |

TABLE 1-continued
| No. | Chemical Structure | Sex Hormone | Linker |
|---|---|---|---|
| XII | 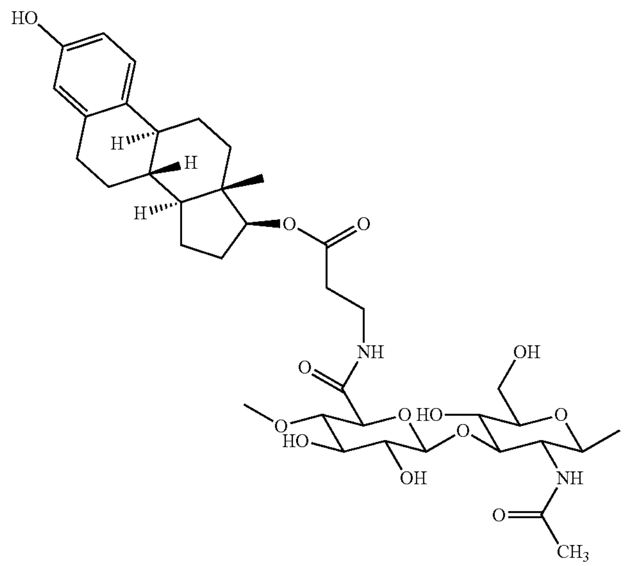 | E2 | β-Ala |
| XIII | 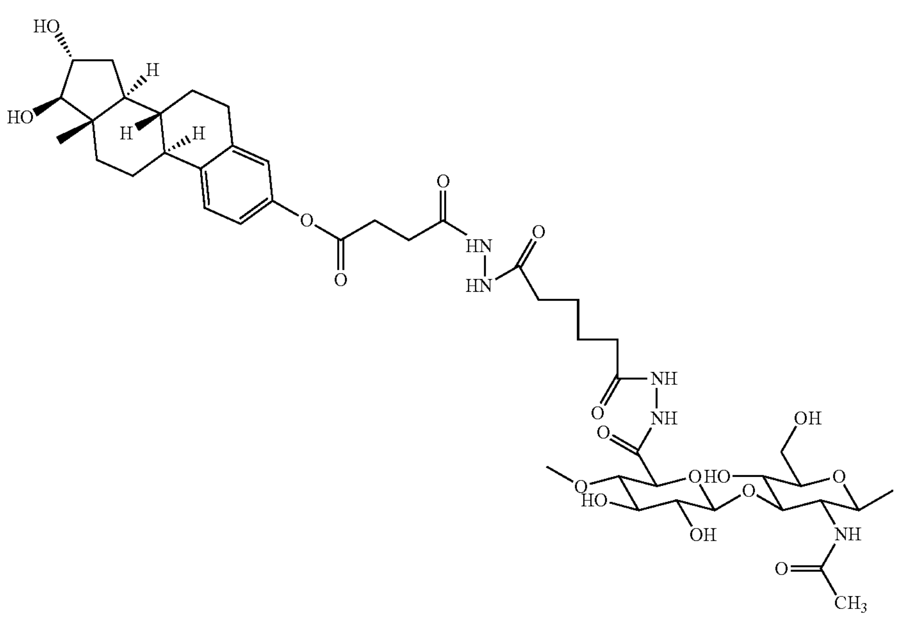 | E3 | ADH-succinate |
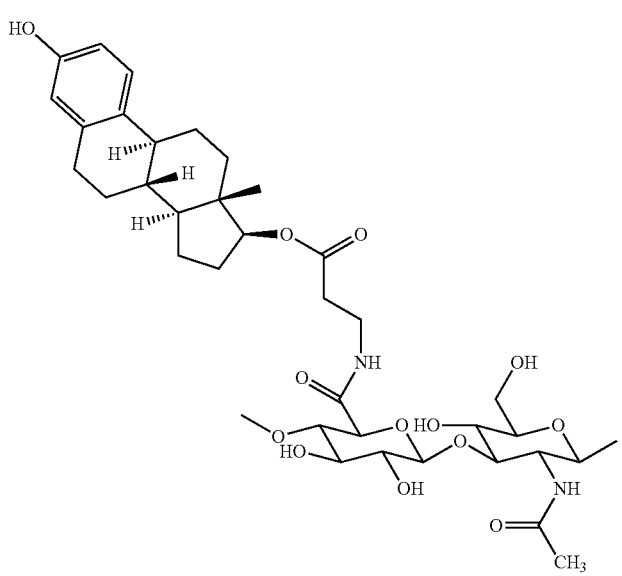
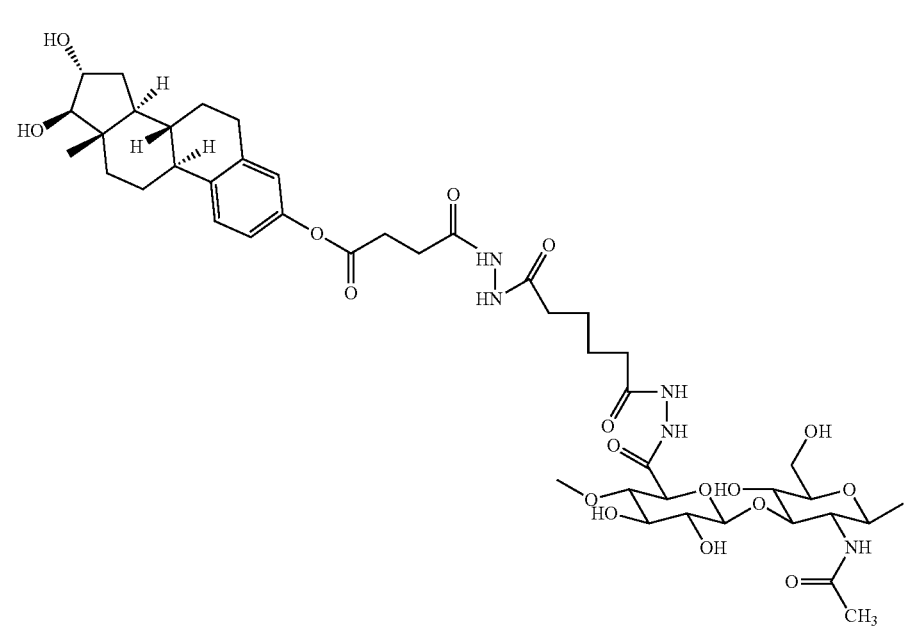

TABLE 1-continued

| No. | Chemical Structure | Sex Hormone | Linker |
|---|---|---|---|
| XIV | 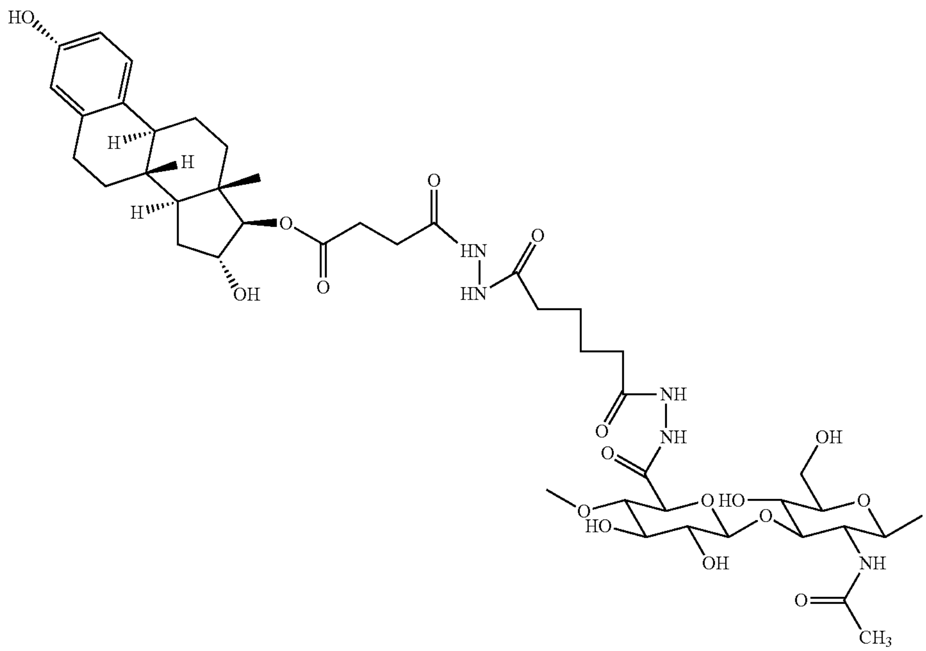 | E3 | ADH-succinate |
| XV | 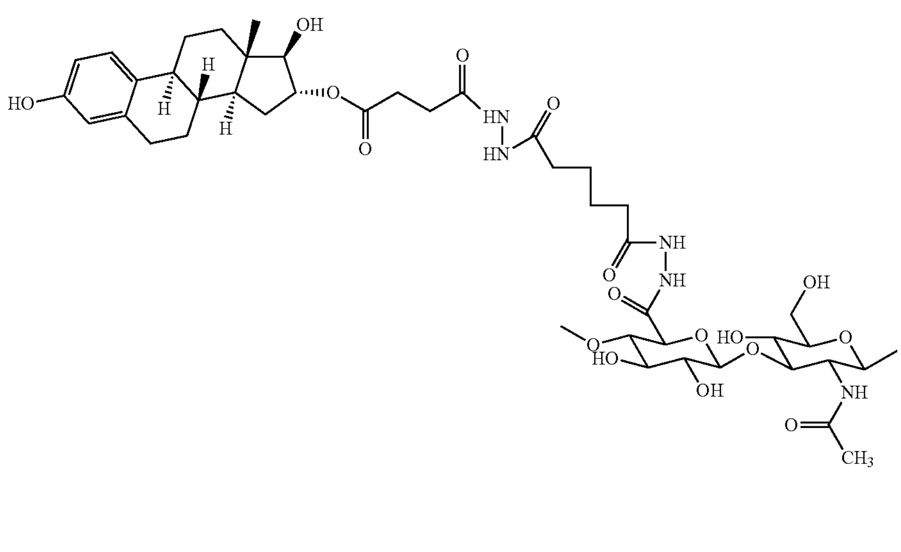 | E3 | ADH-succinate |

TABLE 1-continued

| No. | Chemical Structure | Sex Hormone | Linker |
|---|---|---|---|
| XVI | 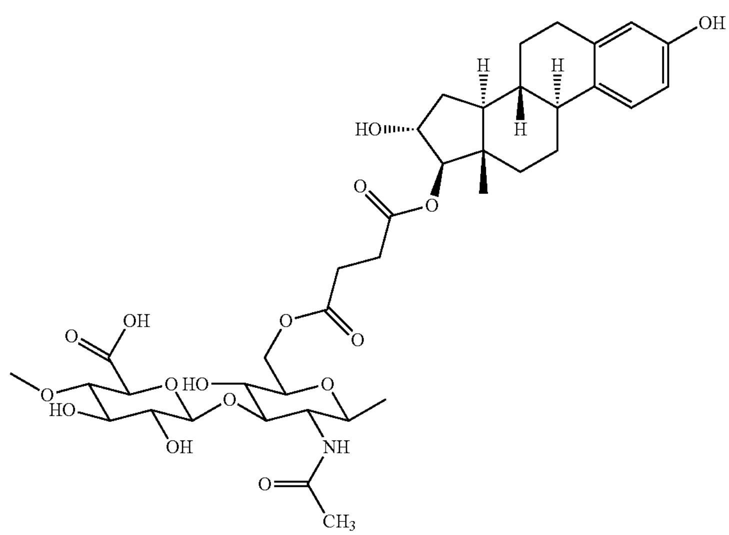 | E3 | Succinate |
| XVII | 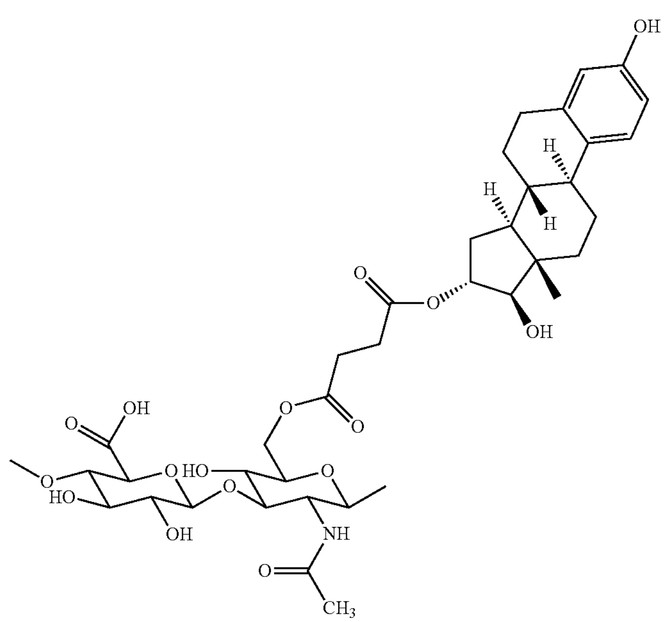 | E3 | Succinate |

TABLE 1-continued
| No. | Chemical Structure | Sex Hormone | Linker |
|---|---|---|---|
| XVIII | 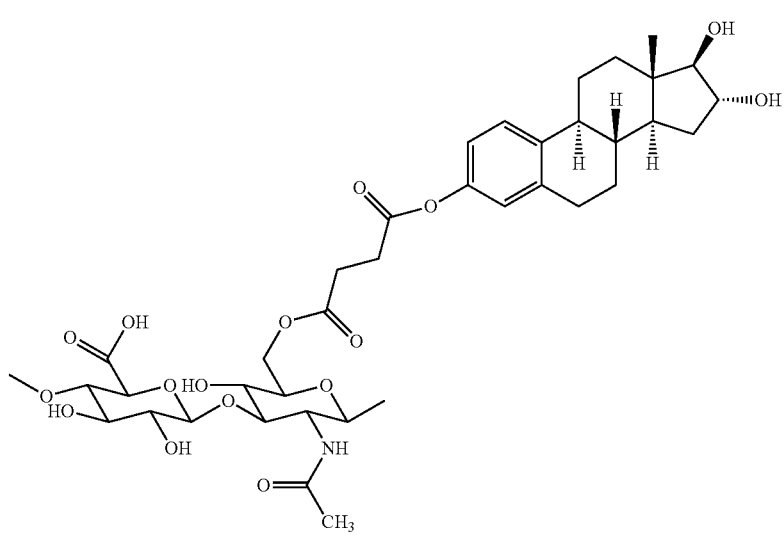 | E3 | Succinate |
| XIX | 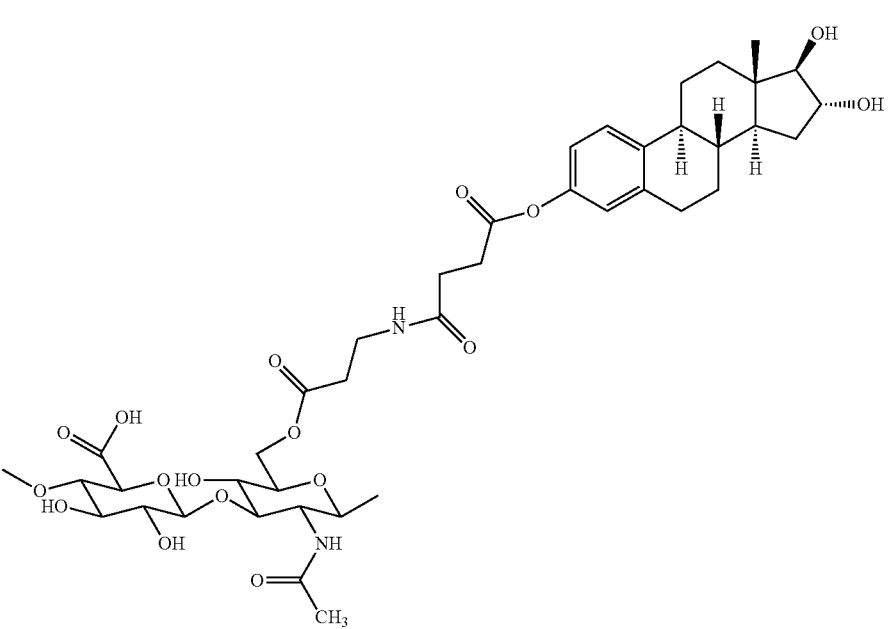 | E3 | β-Ala-succinate |

TABLE 1-continued

| No. | Chemical Structure | Sex Hormone | Linker |
|---|---|---|---|
| XX | 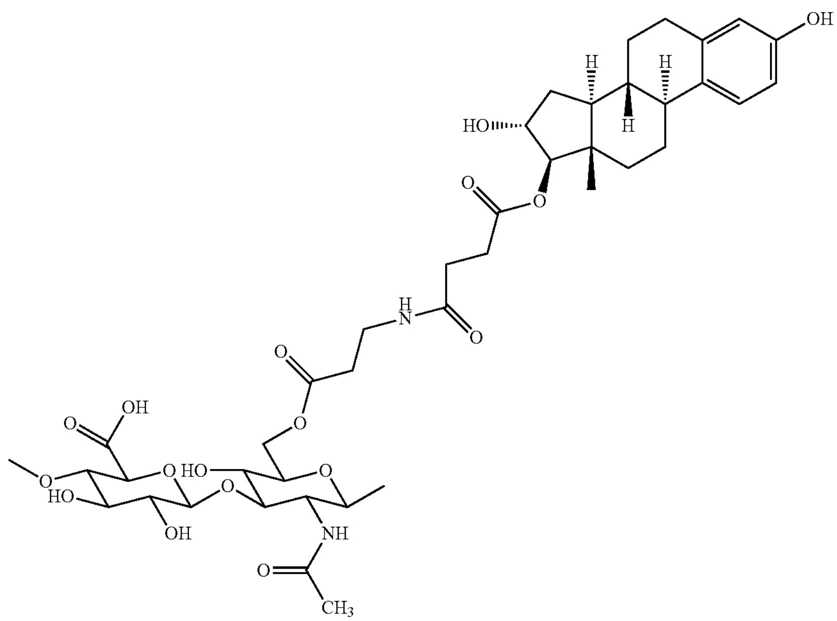 | E3 | β-Ala-succinate |
| XXI | 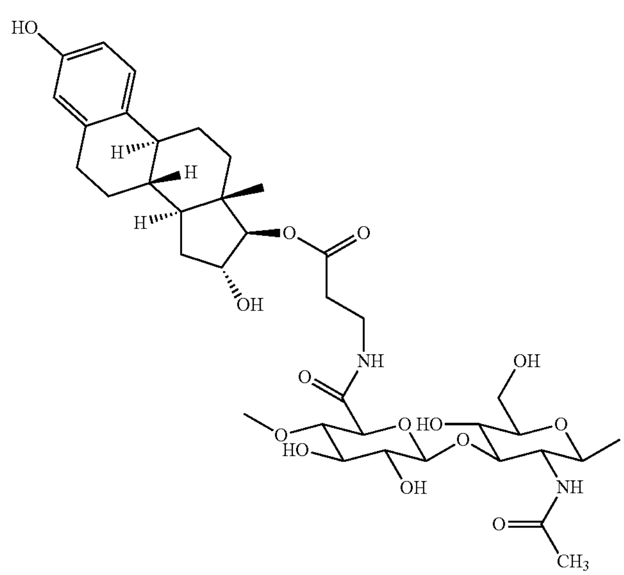 | E3 | β-Ala |

TABLE 1-continued
| No. | Chemical Structure | Sex Hormone | Linker |
|---|---|---|---|
| XXII | 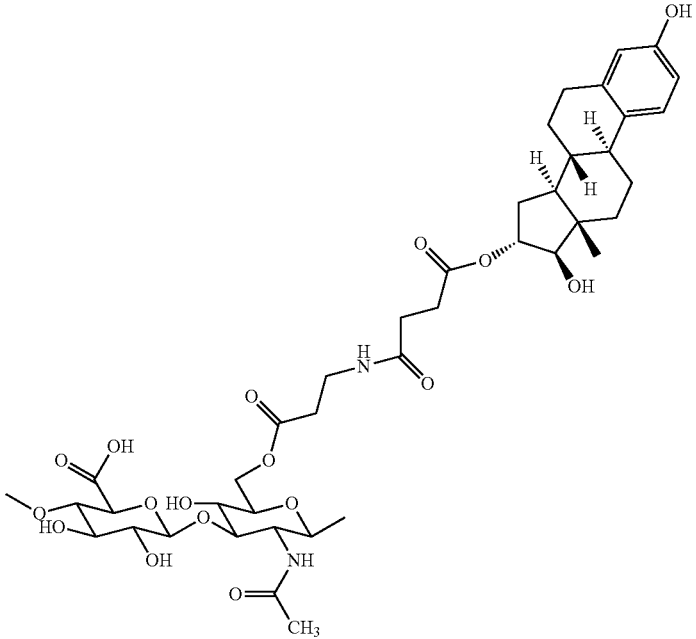 | E3 | β-Ala-succinate |
| XXIII | 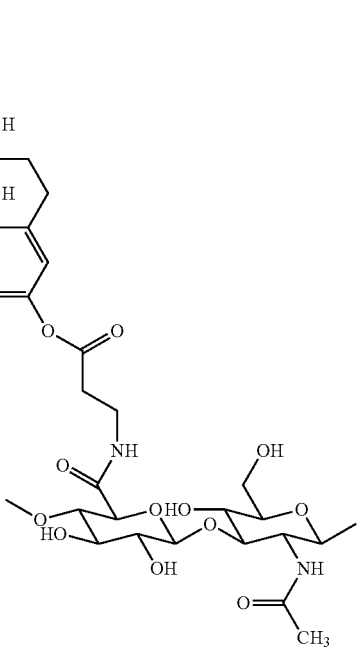 | E3 | β-Ala |

TABLE 1-continued
| No. | Chemical Structure | Sex Hormone | Linker |
|---|---|---|---|
| XXIV | 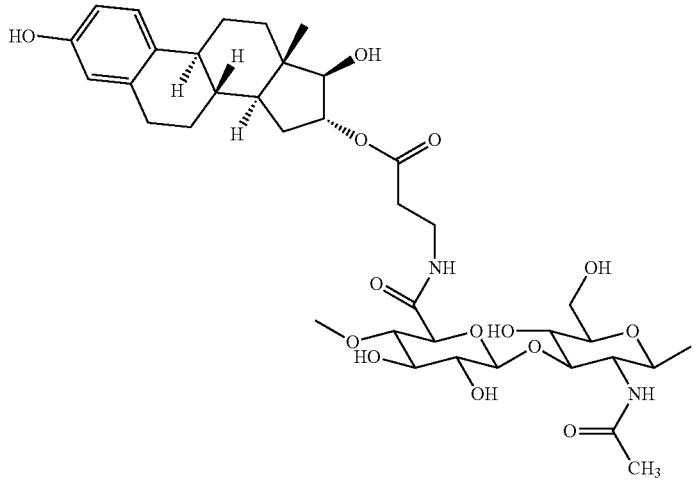 | E3 | β-Ala |
| XXV | 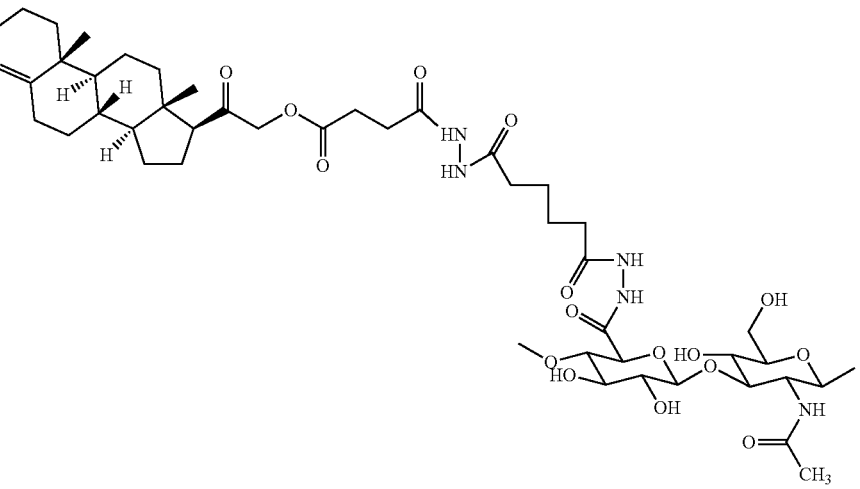 | 11-DOC | ADH-succinate |
| XXVI | 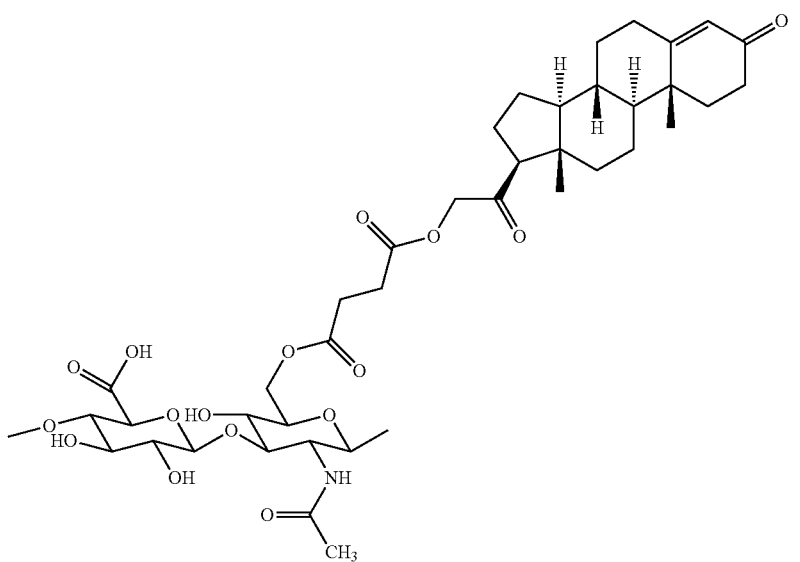 | 11-DOC | Succinate |

TABLE 1-continued

| No. | Chemical Structure | Sex Hormone | Linker |
|---|---|---|---|
| XXVII | 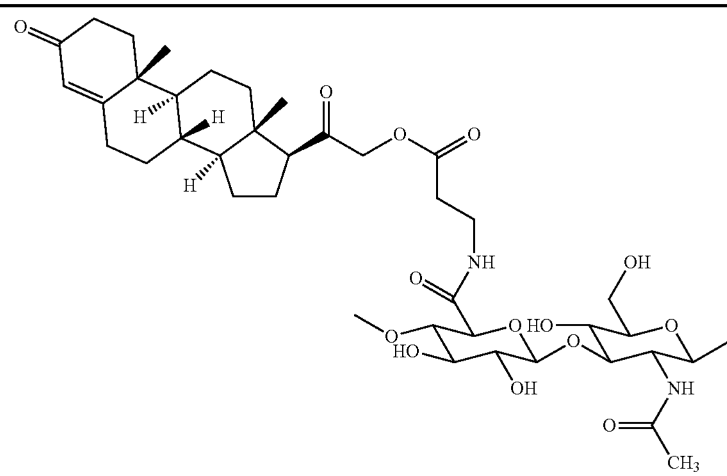 | 11-DOC | β-Ala |
| XXVIII | 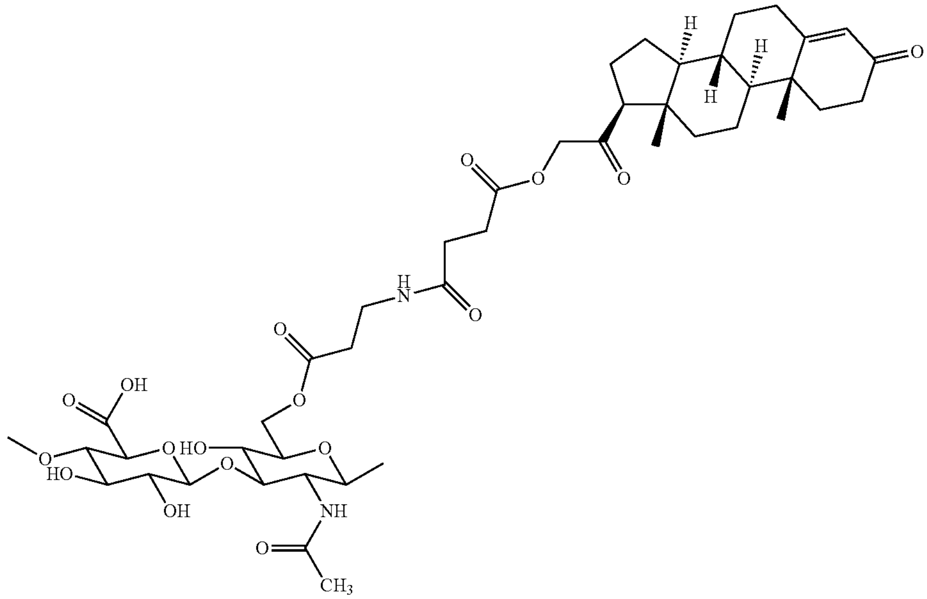 | 11-DOC | β-Ala-succinate |
| XXIX | 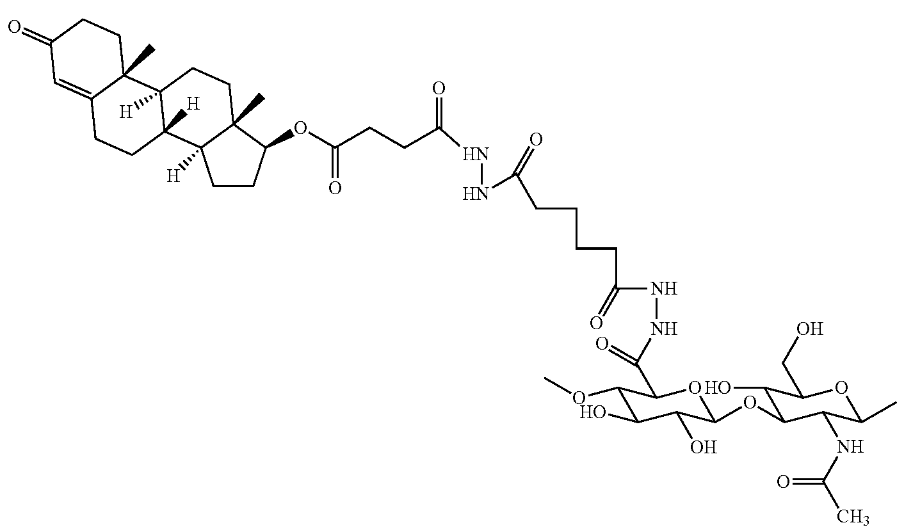 | T | ADH-succinate |

TABLE 1-continued
| No. | Chemical Structure | Sex Hormone | Linker |
|---|---|---|---|
| XXX | 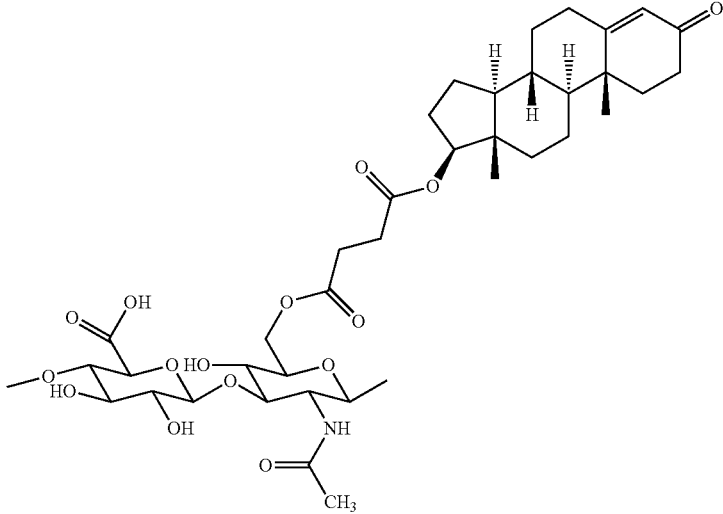 | T | Succinate |
| XXXI | 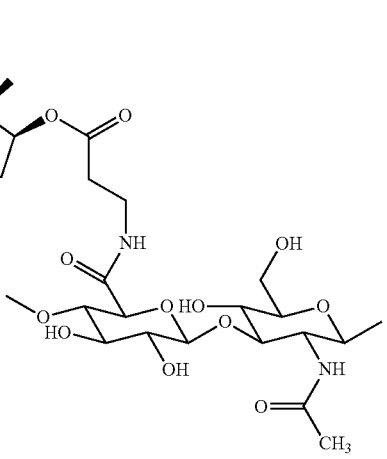 | T | β-Ala |
| XXXII | 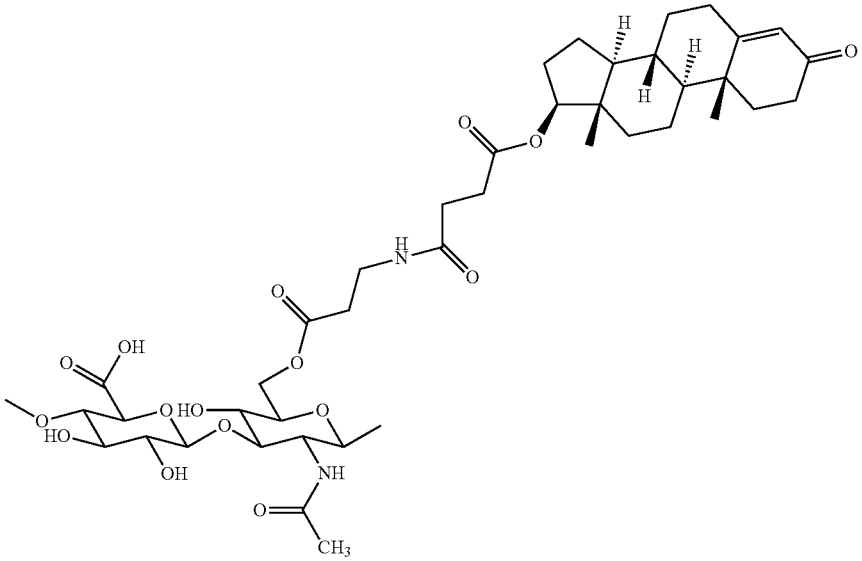 | T | β-Ala-succinate |

According to various embodiments of the present disclosure, the linker has one functional group reactable with the hydroxyl group of the sex hormone and another functional group reactable with the carboxylate group or the hydroxyl group of one disaccharide unit of the HA, thereby conjugating the sex hormone with the HA. However, the present invention is not limited thereto. In other embodiments, the sex hormone may be first modified with a chemical moiety reactable with the linker.

Also encompassed within the present disclose is a composition which comprises the present hyaluronan conjugate described above; and a pharmaceutically-acceptable excipient.

Acceptable carriers are nontoxic to recipients at the dosages and concentrations used. According to some embodiments of the present disclosure, the pharmaceutically-acceptable excipient may comprise buffers such as phosphate, citrate, and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; benzoates, sorbate and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, serine, alanine or lysine; monosaccharides, disaccharides, and other carbohydrates including glucose, mannose, or dextrans; chelating agents such as EDTA; sugars such as sucrose, mannitol, trehalose or sorbitol; salt-forming counter-ions such as sodium; metal complexes (e.g., Zn-protein complexes); and/or non-ionic surfactants such as Tween™, Pluronics™ or polyethylene glycol (PEG) (See Remington: The Science and Practice of Pharmacy 20th Ed. (2000) Lippincott Williams and Wilkins, Ed. K. E. Hoover).

The pharmaceutical compositions described herein can be in unit dosage forms such as tablets, pills, capsules, powders, granules, gels, or solutions or suspensions, for oral or parenteral administration.

The present hyaluronan conjugate is present in the pharmaceutical composition at a level of about 0.1% to 99% by weight, based on the total weight of the pharmaceutical composition. In some embodiments, the present hyaluronan conjugate is present at a level of at least 1% by weight, based on the total weight of the pharmaceutical composition. In certain embodiments, the present hyaluronan conjugate is present at a level of at least 5% by weight, based on the total weight of the pharmaceutical composition. In still other embodiments, the present hyaluronan conjugate is present at a level of at least 10% by weight, based on the total weight of the pharmaceutical composition. In still yet other embodiments, the present hyaluronan conjugate is present at a level of at least 25% by weight, based on the total weight of the pharmaceutical composition.

Pharmaceutical compositions described herein can be prepared by any method known in the art of pharmacology. In general, such preparatory methods include bringing the present hyaluronan conjugate described herein (i.e., the "active ingredient") into association with a carrier or excipient, and/or one or more other accessory ingredients, and then, if necessary and/or desirable, shaping, and/or packaging the product into a desired single- or multi-dose unit. A "unit dose" is a discrete amount of the pharmaceutical composition comprising a predetermined amount of the active ingredient. The amount of the active ingredient is generally equal to the dosage of the active ingredient which would be administered to a subject and/or a convenient fraction of such a dosage, such as one-half or one-third of such a dosage.

The present hyaluronan conjugate provided herein is typically formulated in dosage unit form for ease of administration and uniformity of dosage. It will be understood, however, that the total daily usage of the compositions described herein will be decided by a physician within the scope of sound medical judgment. The specific therapeutically effective dose level for any particular subject or organism will depend upon a variety of factors including the disease being treated and the severity of the disorder; the activity of the specific active ingredient employed; the specific composition employed; the species, age, body weight, general health, sex, and diet of the subject, severity of the side effects or disorder; the time of administration, route of administration, and rate of excretion of the specific active ingredient employed; the duration of the treatment; drugs identity of the particular present hyaluronan conjugates used in combination or coincidental with the specific active ingredient employed; and like factors well known in the medical arts.

As such, also encompassed within the scope of the present disclosure is the use of the present hyaluronan conjugates in manufacturing a pharmaceutical composition, wherein the pharmaceutical composition is used for treating a neurodegenerative disease in a subject in need.

Another aspect of the present disclosure is to provide a method for treating or reducing the risk of a neurodegenerative disease in a subject, comprising the step of administering to the subject an effective amount of the aforementioned hyaluronan conjugate or a pharmaceutical composition comprising the same.

The present hyaluronan conjugates described herein are useful in treating or reducing the risk for a neurodegenerative disease in a subject (e.g., a human patient having, suspected of having, or at risk for the neurodegenerative disease). In some embodiments, the neurodegenerative diseases include, but are not limited to, Alzheimer's disease, Parkinson's disease, amyotrophic lateral sclerosis, multiple sclerosis, Huntington's disease, frontotemporal dementia, epilepsy, neuropathic pain, or ataxia.

The present hyaluronan conjugates provided herein, or a composition comprising such, can be administered by a suitable route as known to those skilled in the art, including oral, nasal, intracranial, intraspinal, intrathecal, intramedullary, intracerebral, intracerebroventricular, intravenous, intraarterial, intracardial, intracutaneous, subcutaneous, transdermal, intraperitoneal, or intramuscular administration. Specifically contemplated routes include oral administration, intravenous administration (e.g., systemic intravenous injection), regional administration via blood and/or lymph supply, and/or direct administration to an affected site. In general, the most appropriate route of administration will depend upon a variety of factors including the nature of the agent (e.g., its stability in the environment of the gastrointestinal tract), and/or the condition of the subject (e.g., whether the subject is able to tolerate oral administration).

The exact amount of the present hyaluronan conjugates or a pharmaceutical composition comprising such required to achieve an effective amount will vary from subject to subject, depending, for example, on factors as described above. An effective amount may be included in a single dose (e.g., single oral dose) or multiple doses (e.g., multiple oral doses). In certain embodiments, when multiple doses are administered to a subject, the frequency of administering the multiple doses to the subject is three doses a day, two doses a day, one dose a day, one dose every other day, one dose every third day, one dose every week, one dose every other week, one dose monthly or one dose every other month. In certain embodiments, the frequency of administering the multiple doses to the subject is one dose per day. In certain embodiments, the frequency of administering the multiple doses to the subject is two doses per day. In certain embodiments, when multiple doses are administered to a subject, the duration between the first dose and last dose of the multiple doses is one day, two days, four days, one week, two weeks, three weeks, one month, two months, three months, four months, six months, nine months, one year, two years, three years, four years, five years, seven years, ten years, fifteen years, twenty years, or the lifetime of the subject. In certain embodiments, the duration between the first dose and last dose of the multiple doses is three months, six months, or one year. In certain embodiments, the duration between the first dose and last dose of the multiple doses is the lifetime of the subject. In a specific embodiment, the frequency of administering the multiple doses to the subject is three doses per week.

For example, according to some working examples of the present disclosure, the effective amount expressed as the equivalent mass of the sex hormone in the hyaluronan conjugate for treating various neurodegenerative diseases in rats (about 150 grams) is about 100 ng/kg body weight to 10 µg/kg body weight. Therefore, the effective amount for treating rats in terms of the sex hormone in the hyaluronan conjugate is about 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 210, 220, 230, 240, 250, 260, 270, 280, 290, 300, 310, 320, 330, 340, 350, 360, 370, 380, 390, 400, 410, 420, 430, 440, 450, 460, 470, 480, 490, 500, 510, 520, 530, 540, 550, 560, 570, 580, 590, 600, 610, 620, 630, 640, 650, 660, 670, 680, 690, 700, 710, 720, 730, 740, 750, 760, 770, 780, 790, 800, 810, 820, 830, 840, 850, 860, 870, 880, 890, 900, 910, 920, 930, 940, 950, 960, 970, 980, or 990 ng/kg body weight/dose, or 1, 1.5, 2, 2.5, 3, 3.5, 4, 4.5, 5, 5.5, 6, 6.5, 7, 7.5, 8, 8.5, 9, 9.5, or 10 µg/kg body weight/dose.

Also, the effective amount for treating mice (about 20 grams) in terms of the equivalent mass of the sex hormone in the hyaluronan conjugate is about 150 ng/kg body weight to 15 µg/kg; for example, about 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 210, 220, 230, 240, 250, 260, 270, 280, 290, 300, 310, 320, 330, 340, 350, 360, 370, 380, 390, 400, 410, 420, 430, 440, 450, 460, 470, 480, 490, 500, 510, 520, 530, 540, 550, 560, 570, 580, 590, 600, 610, 620, 630, 640, 650, 660, 670, 680, 690, 700, 710, 720, 730, 740, 750, 760, 770, 780, 790, 800, 810, 820, 830, 840, 850, 860, 870, 880, 890, 900, 910, 920, 930, 940, 950, 960, 970, 980, or 990 ng/kg body weight/dose, or 1, 1.5, 2, 2.5, 3, 3.5, 4, 4.5, 5, 5.5, 6, 6.5, 7, 7.5, 8, 8.5, 9, 9.5, 10, 10.5, 11, 11.5, 12, 12.5, 13, 13.5, 14, 14.5, or 15 µg/kg body weight/dose.

In an adult human weighting approximately 60 kg, the human equivalent dose (HED) derived from the above-described doses for rats (conversion factor: 0.16) is about 16 ng/kg body weight to 1.6 µg/kg body weight/dose, in terms of the equivalent mass of the sex hormone in the hyaluronan conjugate. On the other hand, the HED based on the mice dose (conversion factor: 0.08) is about 12 ng/kg body weight to 1.2 µg/kg body weight/dose. In sum, the HED is about 12 ng/kg body weight to 1.6 µg/kg body weight/dose, in terms of the equivalent mass of the sex hormone in the hyaluronan conjugate.

As could be appreciated, the dosage ranges described above is provided as a guidance for the administration of provided pharmaceutical compositions to an adult. The amount to be administered to, for example, a child or an adolescent can be determined by a medical practitioner or person skilled in the art and can be lower or the same as that administered to an adult. Considering the age, weight, and health condition of the patient, the effective amount for a human subject can be about 6 ng/kg body weight/dose to 3 µg/kg body weight/dose, in terms of the equivalent mass of the sex hormone in the hyaluronan conjugate. Specifically, the effective amount of the equivalent mass of the sex hormone in the present hyaluronan conjugate for a human subject may be 6, 6.5, 7, 7.5, 8, 8.5, 9, 9.5, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 210, 220, 230, 240, 250, 260, 270, 280, 290, 300, 310, 320, 330, 340, 350, 360, 370, 380, 390, 400, 410, 420, 430, 440, 450, 460, 470, 480, 490, 500, 510, 520, 530, 540, 550, 560, 570, 580, 590, 600, 610, 620, 630, 640, 650, 660, 670, 680, 690, 700, 710, 720, 730, 740, 750, 760, 770, 780, 790, 800, 810, 820, 830, 840, 850, 860, 870, 880, 890, 900, 910, 920, 930, 940, 950, 960, 970, 980, or 990 ng/kg body weight/dose, or 1, 1.5, 2, 2.5, or 3 µg/kg body weight/dose.

As could be appreciated by persons having ordinary skill in the art, the effective amount of the present hyaluronan conjugate for treating various neurodegenerative can be determined from the above-mentioned equivalent mass of the sex hormone in the hyaluronan conjugate in conjunction with the drug load (or the degree of substitution) of the hyaluronan conjugate. And each of the effective amounts of the present hyaluronan conjugate thus determined is deemed to be part of the present disclosure.

For example, according to some working examples of the present disclosure, the effective amount of the hyaluronan conjugate for treating various neurodegenerative diseases in rats (about 150 grams) is about 25 to 2,500 µg/kg body weight, and in mice (about 20 grams) is about 1 to 100 µg/kg. Therefore, the effective amount of the present hyaluronan conjugate for treating neurodegenerative diseases in rats is about 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 210, 220, 230, 240, 250, 260, 270, 280, 290, 300, 310, 320, 330, 340, 350, 360, 370, 380, 390, 400, 410, 420, 430, 440, 450, 460, 470, 480, 490, 500, 510, 520, 530, 540, 550, 560, 570, 580, 590, 600, 610, 620, 630, 640, 650, 660, 670, 680, 690, 700, 710, 720, 730, 740, 750, 760, 770, 780, 790, 800, 810, 820, 830, 840, 850, 860, 870, 880, 890, 900, 910, 920, 930, 940, 950, 960, 970, 980, 990, 1000, 1100, 1200, 1300, 1400, 1500, 1600, 1700, 1800, 1900, 2000, 2100, 2200, 2300, 2400, or 2500 µg/kg body weight/dose. Also, the effective amount of the present hyaluronan conjugate for treating mice is about 1, 1.5, 2, 2.5, 3, 3.5, 4, 4.5, 5, 5.5, 6, 6.5, 7, 7.5, 8, 8.5, 9, 9.5, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100 µg/kg body weight/dose.

Similarly, in an adult human weighting approximately 60 kg, the HED of the present hyaluronan conjugate derived from the above-described doses for mice (conversion factor: 0.08) is about 80 ng/kg body weight/dose to 8 µg/kg body weight/dose, and for rat (conversion factor: 0.16), 4 to 400 µg/kg body weight/dose. In sum, the HED for the present hyaluronan conjugate is about 80 ng/kg body weight to 400 µg/kg body weight/dose. Considering the age, weight, and health condition of the patient, the effective amount for a human subject can be about 40 ng/kg body weight/dose to 700 µg/kg body weight/dose.

Specifically, the effective amount for a human subject may be 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 210, 220, 230, 240, 250, 260, 270, 280, 290, 300, 310, 320, 330, 340, 350, 360, 370, 380, 390, 400, 410, 420, 430, 440, 450, 460, 470, 480, 490, 500, 510, 520, 530, 540, 550, 560, 570, 580, 590, 600, 610, 620, 630, 640, 650, 660, 670, 680, 690, 700, 710, 720, 730, 740, 750, 760, 770, 780, 790, 800, 810, 820, 830, 840, 850, 860, 870, 880, 890, 900, 910, 920, 930, 940, 950, 960, 970, 980, or 990 ng/kg body weight/dose, or 1, 1.5, 2, 2.5, 3, 3.5, 4, 4.5, 5, 5.5, 6, 6.5, 7, 7.5, 8, 8.5, 9, 9.5, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 210, 220, 230, 240, 250, 260, 270, 280, 290, 300, 310, 320, 330, 340, 350, 360, 370, 380, 390, 400, 410, 420, 430, 440, 450, 460, 470, 480, 490, 500, 510, 520, 530, 540, 550, 560, 570, 580, 590, 600, 610, 620, 630, 640, 650, 660, 670, 680, 690, or 700 µg/kg body weight/dose.

Dose ranges as described herein provide guidance for the administration of provided pharmaceutical compositions to an adult. The amount to be administered to, for example, a child or an adolescent can be determined by a medical practitioner or person skilled in the art and can be lower or the same as that administered to an adult.

The present hyaluronan conjugate, as described herein, can be administered in combination with one or more additional pharmaceutical agents (e.g., therapeutically active agents) useful in treating and/or reducing the risk for a neurodegenerative disease. In certain embodiments, the present hyaluronan conjugate described herein and the additional pharmaceutical agent show a synergistic effect on treating a neurodegenerative disease. The present hyaluronan conjugate can be administered concurrently with, prior to, currently with, or subsequent to one or more additional pharmaceutical agents, which may be useful as, e.g., combination therapies in treating and/or reducing the risk for a neurodegenerative disease in a subject.

Pharmaceutical agents include therapeutically active agents. Each additional pharmaceutical agent may be administered at a dose and/or on a time schedule determined for that pharmaceutical agent. The additional pharmaceutical agents may also be administered together with each other and/or with the composition comprising the present hyaluronan conjugate described herein in a single dose or administered separately in different doses. In certain embodiments, the additional pharmaceutical agent is an agent for treating and/or reducing the risk for a neurodegenerative disease can be an agent for treating Alzheimer's disease (AD), includes, but is not limited to, donepezil, rivastigmine, galantamine, memantine, selfotel, midafotel, tacrine, selegiline, and vitamin E.

According to some embodiments of the present disclosure, the subject treatable by the present hyaluronan conjugate is a mammal. In some examples, the subject is a mouse or a rat. In other examples, the subject is a human.

Also encompassed by the present disclosure are kits for use in treating any of the target neurodegenerative diseases described herein. The kits provided herein may comprise the present hyaluronan conjugates described herein, or a pharmaceutical composition comprising such. Optionally, the kit may further comprise one or more additional pharmaceutical agents as described herein.

The following Examples are provided to elucidate certain aspects of the present invention and to aid those of skilled in the art in practicing this invention. These Examples are in no way to be considered to limit the scope of the invention in any manner. Without further elaboration, it is believed that one skilled in the art can, based on the description herein, utilize the present invention to its fullest extent. All publications cited herein are hereby incorporated by reference in their entirety.

EXAMPLES

Example 1

Synthesis and characterization of HA-βALA-Estradiol

In this example, a mixture containing both HA-βALA-C17 estradiol (A form) and HA-βALA-C3 estradiol (B form) was synthesized in accordance with steps described in Scheme I (FIG. 1).

Briefly, Boc-β-alanine (2.92 mmole, 552 mg), DCC (3.40 mmole, 702 mg), and 4-dimethylaminopyridine (DMAP) (3.04 mmole, 372 mg) were added into a solution of estradiol (2.75 mmole, 750 mg) in dichloromethane (DCM) (250 mL), and the mixture was stirred overnight at room temperature (RT). The solvent was removed under vacuum and the precipitate was then dissolved by methanol. The resulting mixture was added with 10% $K_2CO_3$ solution (methanol:10% $K_2CO_3$=1:1) and stirred overnight at RT. Then, the mixture was concentrated and extracted by DCM and water. Most DCM within the mixture was removed under vacuum, and the precipitate within the mixture was filtered out. The filtrate was washed by DCM and concentrated under vacuum. The residue was washed by acetone, and the precipitate was filtered out. After that, the filtrate was concentrated, and then purified by silica gel column chromatography (eluent: acetone:hexane=1:1) to obtain the product, Boc-β-alanine-estradiol.

The stepwise procedure for the synthesis of HA-βALA-Estradiol was as follows: A bottle: Boc-β-alanine-estradiol (0.19 mmole, 83 mg) was dissolved in DCM (1 mL), and the solution was stirred at RT. The solution was added with trifluoroacetic acid (TFA) (0.2 mL, 2 mmole), and the reaction lasted for 4 hours; then $Na_2CO_3$ solution (55 mg/mL) was added dropwisely into the solution in ice bath until no bubble was released from the solution. Then, DCM was removed from the solution under vacuum. Ethyl cyanohydroxyiminoacetate (oxyma) (1.39 mmole, 250 mg) and dimethyl sulfoxide (DMSO) (20 mL) were then added to the residue, and the solution was stirred at RT. B bottle: HA solution (500 mg/25 mL) was mixed with DMSO (20 mL), and the mixture was stirred until the temperature went back to RT. The solution of B bottle was poured into A bottle, and the mixture was thoroughly mixed. N,N'-diisopropylcarbodiimide (DIC) (2.58 mmole, 326 mg) was added into the mixture under the level, and the reaction was lasted for 24 hours. After that, the reaction mixture was purified by dialysis (3500 molecular weight cut off (MWCO) dialysis bag, 10 L of water for 12 hours; 1 L of 0.3M NaCl for 12 hours, twice; and 10 L of water for 12 hours, 5 times), and then the fraction within the dialysis bag was collected and lyophilized.

The HA-βALA-C3/C17 estradiol (HA-E2) thus synthesized was confirmed by UPLC (Acquity UPLC and PDA detector (Waters)); column: ACQUITY UPLC BEH200 SEC column (1.7 μm, ID 4.6 mm×150 mm); flow rate: 0.3 mL/min; injection volume: 50 μl; detector: UV 280 nm; temperature: for column, 25° C., for autosampler, 20° C.; running time: 18 minutes; relative retention time: for HA-E2 (HA-βALA-C3/C17 estradiol), 2.7, for E2 (estradiol), 10.1. For calculation, linear regression was applied to generate a standard curve y=mx+b, wherein: x is E2 concentration in μg/ml; y is the peak area for all standards; m is the slope of standard curve; b is the intercept of standard curve; and, acceptable correlation coefficient (r2) for standard curve is ≥0.9950.

Figure 2A:
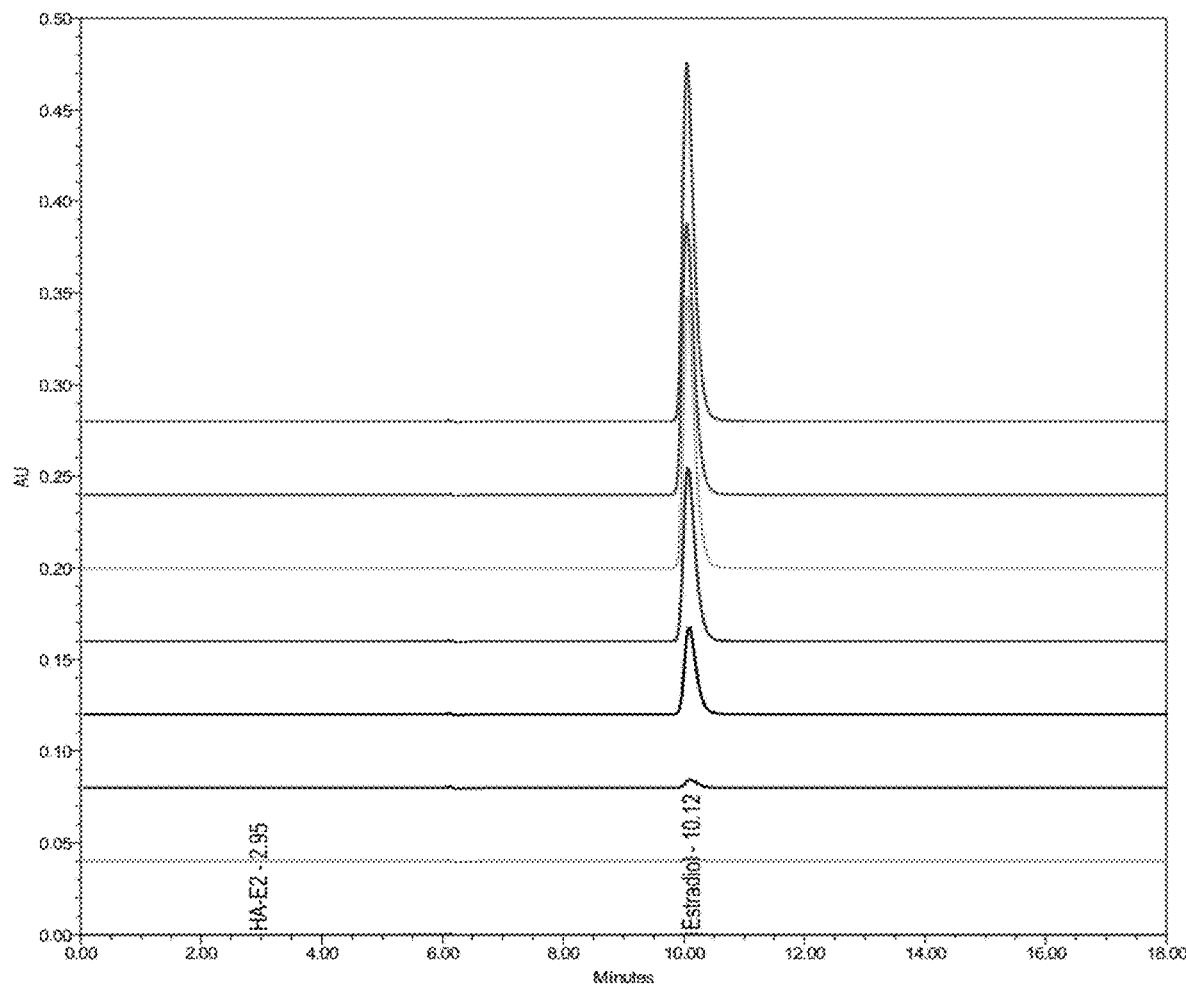
FIG. 2A and FIG. 2B show UPLC analysis results of estradiol (E2) and HA-E2, respectively, according to one working example of the present disclosure.
Figure 2B:
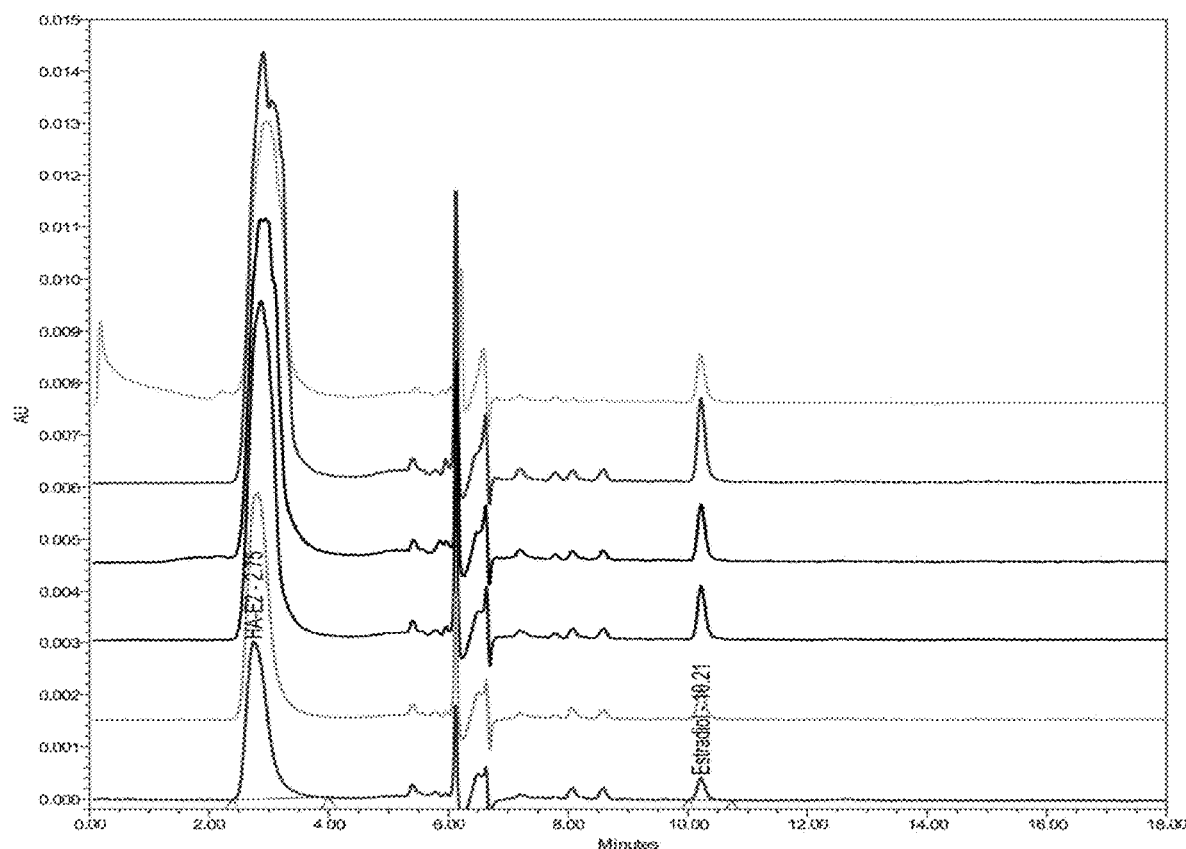

FIG. 2A and FIG. 2B respectively show the UPLC profile of estradiol (E2) and HA-βALA-C3/C17 estradiol (HA-E2).

Example 2

Effect of Hyaluronan Conjugates on Neural Cell Uptake

In this example, paired set of experiments were performed to investigate the neural cell (human neuroblastoma SH-SY5Y cells) uptake of the present hyaluronan conjugates. The results (data not shown) indicate that the neural cells uptake more HA-E1 conjugate than estrone alone, the same also applies to other paired sets, including, HA-E2 conjugate vs estradiol alone, HA-E3 conjugate vs estriol alone, HA-testosterone conjugate vs testosterone alone, and HA-deoxycorticosterone vs 11-deoxycorticosterone alone.

Based on the preliminary results from the paired-set experiments above, HA-E2 and E2 were subject to further analysis.

It is known that estrogen can help maintain the viability of neural cells, and one manifestation of this phenomenon is the upregulation of ATP level in cells. Since mitochondrial membrane potential is the driving force for mitochondrial ATP synthesis, neural cells were respectively treated with HA-C17-E2 and E2, and the cellular mitochondrial membrane potential level was then measured.

Briefly, human neuroblastoma SH-SY5Y cells were grown in Eagle's minimum essential medium (EMEM) supplemented with 10% heat-inactivated fetal bovine serum (FBS), 100 units/mL penicillin, and 100 μg/mL streptomycin, at 37° C. in a humidified 5% $CO_2$ incubator. For measurement of mitochondrial membrane potential, SH-SY5Y cells were incubated together with E2 (0.14, 0.34, 0.68, and 1.36 μg/mL), HA (6.48, 16.19, 32.38, and 64.76 μg/mL), or HA-C17-E2 (6.48, 16.19, 32.38, and 64.76 μg/mL, respectively equivalent to the E2 concentration) for 18 hours.

Tetramethylrhodamine, methyl ester (TMRM) is a cell-permeant, cationic, red-orange fluorescent dye that is readily sequestered by active mitochondria. Cells were trypsinized and resuspended in 0.5 mL of PBS containing 100 nM of TMRM (Molecular Probes, Eugene, Oreg.). After incubation for 30 minutes at 37° C. in the dark, cells were immediately transferred to a tube on ice, and the fluorescence intensity was measured by flow cytometry using FL2 detector.

A FACS Calibur flowcytometer (Becton Dickinson, Bedford, Mass.) equipped with a 488-nm argon laser was used for the flow cytometric analysis. Forward and side scatters were used to establish size gates and exclude cellular debris from the analysis. The excitation wavelength was set at 488 nm. In each measurement, a minimum of 20,000 cells were analyzed. Data were acquired and analyzed using the Cell Quest software (Becton Dickinson). Relative change in the mean fluorescence intensity was calculated as the ratio between mean fluorescence intensity in the channel of the treated cells and that of the control cells.

Figure 3:
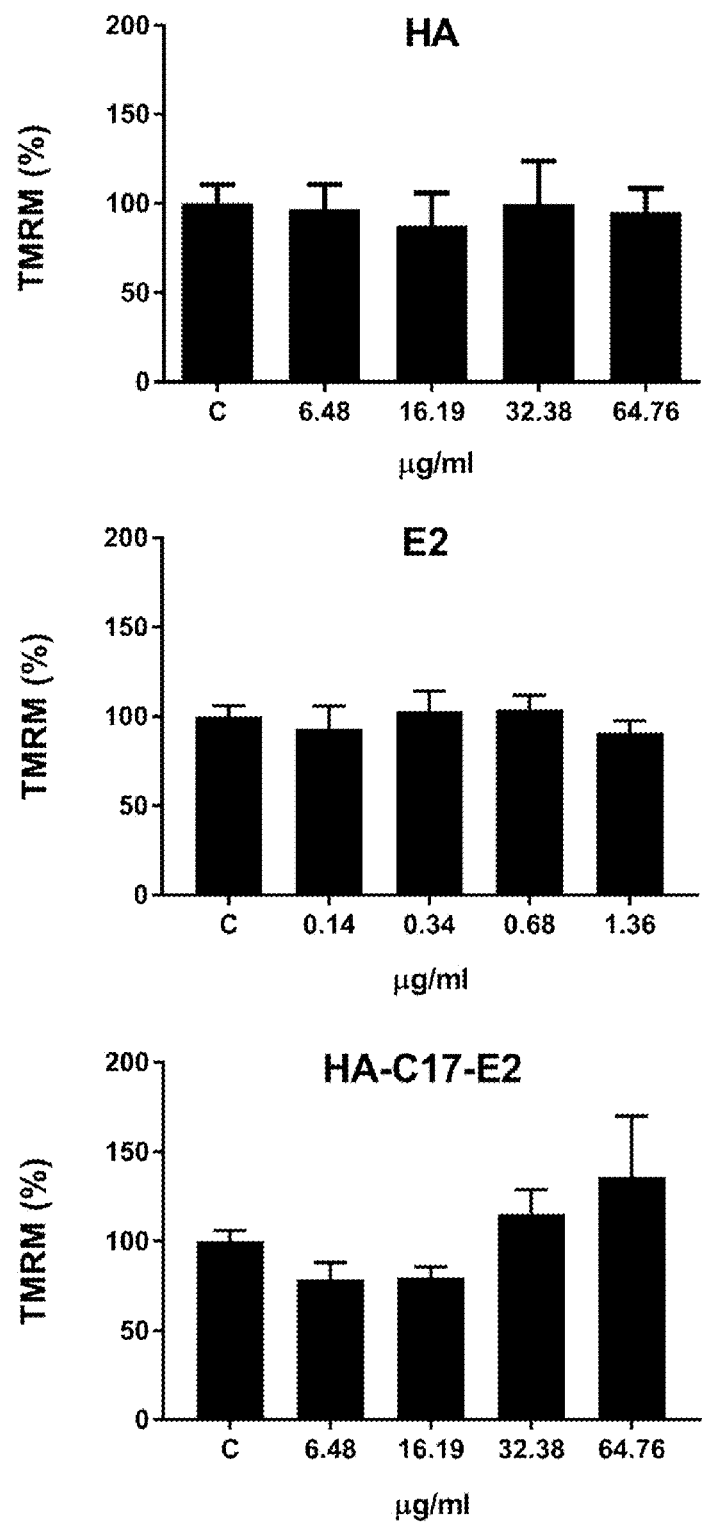
FIG. 3 show the effect of the HA-C17-E2 hyaluronan conjugate on in vitro mitochondrial membrane potential (MMP) levels; according to one working example of the present disclosure.

As shown in FIG. 3, the treatment of HA-C17-E2 (32.38 μg/mL, equivalent to 0.68 μg/mL E2) or HA-C17-E2 (64.76 μg/mL, equivalent to 1.36 μg/mL E2) is capable of increasing the mitochondrial membrane potential levels in cells, compared to the control group and HA only or E2 only treatment.

Example 3

Effect of Hyaluronan Conjugates on Amyloid Beta Expression

In this example, effects of the present hyaluronan conjugate on several indexes of Alzheimer's disease in APP/PS1 transgenic mice including amyloid plaque formation and distribution and expression level of Aβ42, were investigated. APP/PS1 transgenic mice overproduce amyloid beta (Aβ) and are extensively used as the animal model of Alzheimer's disease.

APPswe/PS1dE9 (APP/PS1) transgenic mice were obtained from Jackson lab. All the procedures were performed in accordance with the specifications of the Animal Experimental Center of the National Research Institution of Chinese Medicine (IACUC No. 106-417-4).

The APP/PS1 mice of 8 week-old were intravenously administered 0.206 mg/kg E2 or 12.5 mg/kg HA-E2 (equivalent to 0.206 mg/kg E2) or the control vehicle three times per week, for a total of 8 weeks. On the $7^{th}$ week, 5-bromo-2'-deoxyuridine (BrdU) of a dose of 50 mg/Kg/day was administered intraperitoneally daily for 7 days. The animals were then sacrificed by anesthesia with administered intraperitoneally Zoletil/Xylazine (20 mg/Kg: 5 mg/Kg). After deep anesthesia, blood was collected from the heart, centrifuged at 13,000 rpm to isolate the serum. After perfusion with pH 7.4 saline, the cortex and hippocampus of the hemisphere of the brain were surgically removed, homogenized, and stored at −30° C. The other half of the brain was fixed by immersed in 4% formaldehyde for 3 to 7 days, followed by dehydration with 20% and 30% sucrose for 3 to 7 days. The brain tissues were frozen for further sectioning.

Two-step sequential extraction of the brain Aβ using 2% SDS and 70% formic acid (FA) (Sigma) was performed. Briefly, the cortical homogenate was mixed with an equal volume of 4% SDS in H-buffer containing the protease inhibitor. The samples were then sonicated and centrifuged at 100,000×g at 4° C. for 60 minutes. The supernatant of the samples was the SDS-soluble fraction. For the SDS-insoluble fraction, the pellet of the samples was further re-suspended in 70% FA and centrifuged at 100,000×g at 4° C. for 60 minutes. The supernatant was then collected and neutralized with 1M Tris, pH 11. Both the SDS-soluble and SDS-insoluble fractions were stored at −80° C. until sandwich ELISA analysis. Aβ level was measured by a human Aβ40 and Aβ42 ELISA kit (Invitrogen) according to the manufacturer's protocol.

Figure 4A:
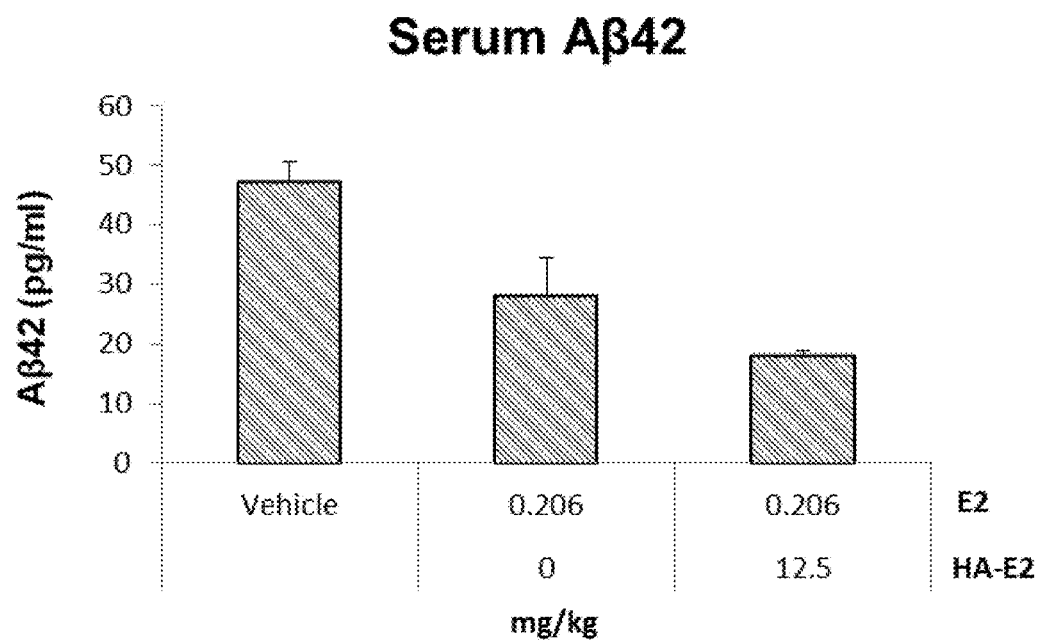
FIG. 4A and FIG. 4B show the effect of the HA-E2 hyaluronan conjugate on in vivo serum and hippocampus Aβ42 level changes in APP/PS1 transgenic mice, respectively, according to one working example of the present disclosure.
Figure 4B:
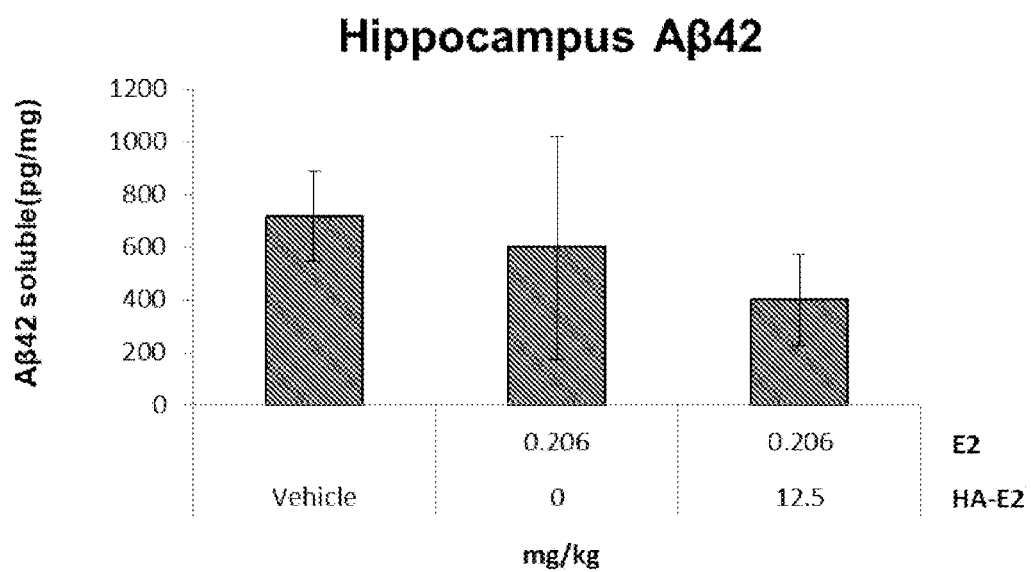

The expression level of Aβ42 in serum and in hippocampus thus determined are summarized in FIG. 4A and FIG. 4B, respectively. The expression levels of Aβ42 in both the serum and hippocampus of mice treated with HA-E2 is lower than those in mice treated with E2 alone or vehicle alone.

Example 4

Synthesis of HA-βALA-C17 Estradiol (HA-C17-E2)

Figure 5:
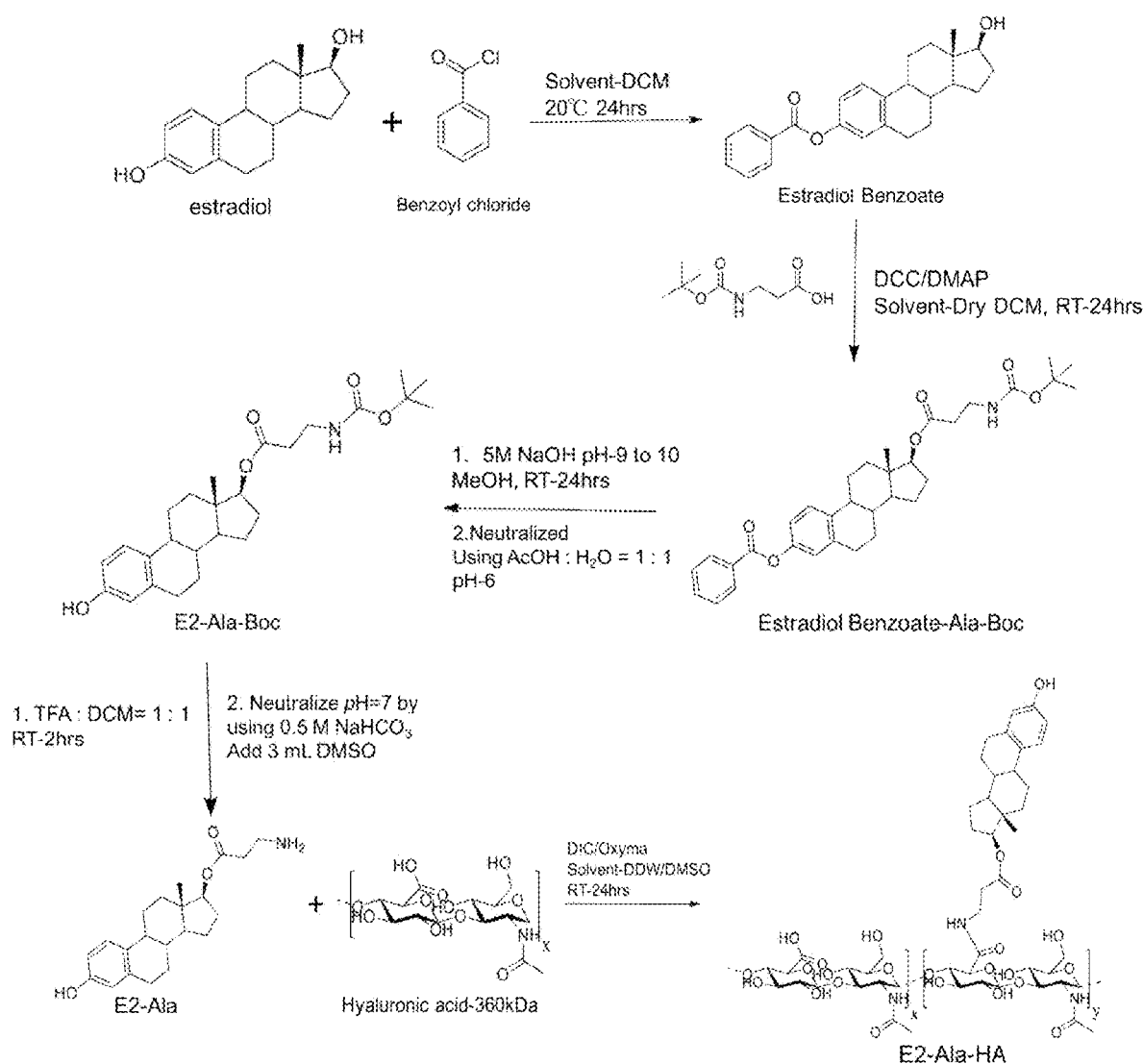
FIG. 5 is scheme for synthesizing the HA-C17-E2 hyaluronan conjugate according to one working example of the present disclosure.

In this example, HA-βALA-C17 estradiol (HA-C17-E2) was synthesized in accordance with Scheme III (FIG. 5).

First, estradiol (1.84 mmole, 500 mg) was dissolved in DCM (40 mL) and stirred for 15 minutes. Then, 255 μL of 2.02 mmole benzoyl chloride and 5 drops of triethylamine were added to the reaction mixture, which was then stirred for 24 hours at 20° C. under nitrogen. The reaction mixture was concentrated under vacuum and then purified using silica gel column chromatography (elution: EA/DCM=3/97) to obtain estradiol benzoate (Bz-estradiol).

Next, Bz-estradiol (0.23 mmole, 85 mg) was dissolved in dry DCM (20 mL) and stirred for 10 minutes. N,N'-Dicyclohexylcarbodiimide (DCC) (0.45 mmole, 94 mg) and 4-dimethylaminopyridine (DMAP) (0.23 mmole, 27 mg) were added in the reaction mixture, which was stirred for 30 minutes. Thereafter, Boc-β-alanine (0.45 mmole, 87 mg) was added and stirred under nitrogen for 24 hours at 25° C. The reaction mixture was filtered and the filtrate was extracted using DDW. The organic layer was collected, and the solvent was removed under vacuum to obtain the crude product, which was then purified using silica gel column chromatography (elution: EA/DCM=3/97) to obtain estradiol-benzoate-Ala-Boc (Bz-Estradiol-β-ALA-boc).

Then, Bz-Estradiol-β-ALA-boc (0.18 mmole, 100 mg) was dissolved in MeOH (5 mL), and the pH was adjusted to 9-10 using 5 M NaOH. The reaction mixture was stirred under room temperature. After 24 hours, the pH of the reaction mixture was adjusted to 6 using 50% AcOH, which was then concentrated to obtain an oily liquid. The oily liquid was extracted three times using EA and brine. The water in the organic layer was removed using MgSO4, and the solvent was then removed under vacuum to obtain the crude product, which was later purified using silica gel column chromatography (elution: EA/DCM=5/95) to obtain E2-Ala-Boc.

The stepwise procedure for the synthesis of HA-C17-E2 was as follows. Bottle A: HA (0.49 mmole, 200 mg) was dissolved in DDW (20 mL) by stirring for 2 hours, and then DMSO (25 mL) was poured into the reaction mixture under stir until the temperature went back to RT. Bottle B: E2-Ala-Boc (0.10 mmole, 44.1 mg) was dissolved in DCM (2 mL) and then added with trifluoroacetic acid (TFA) (1.31 mmole, 0.1 mL). The solution was stirred at RT for 2 hours. Thereafter, most of the DCM and TFA were removed by concentration, and then DDW (2 mL) was poured into the reaction mixture and the pH was adjusted to 7 using 0.5 M NaHCO$_3$. DMSO was added into the reaction mixture until the precipitate dissolved. Oxyma (0.55 mmole, 77 mg) was dissolved in DMSO (4 mL), and the solution was then poured into bottle A, which was then stirred for 10 minutes. The solution of bottle B was slowly added into bottle A by pipette, and the mixture was thoroughly mixed for 15 minutes. DIC (2.58 mmole, 326 mg) was added into the mixture under the level by pipette, and the reaction was lasted for 24 hours. After that, the reaction mixture was purified by dialysis (3,500 MWCO dialysis bag, 5 L of 0.3 M NaCl for 12 hours, 6 times; and 5 L of water for 12 hours, 6 times), and then the fraction within the dialysis bag was collected and lyophilized.

The HA-C17-E2 thus synthesized was confirmed by UPLC (data not shown), and the drug load was determined using UV-Vis spectrometer at 280 nm. In one working example, the DS of the HA-C17-E2 is about 0.54%; in another working example, the DS of the HA-C17-E2 is about 13.55%.

Example 5

Effect of Hyaluronan Conjugates on Cognitive Functions

Prior study has demonstrated that of ovariectomy (OVX) or hysteroovariotomy (OHE) female rats showed a significant decrease in dendritic spine of pyramidal neurons in sensorimotor cortex and the hippocampal CA1 region and manifested cognitive deficits, suggesting that estrogen play some roles in the learning and memory function of rats.

In this examples, female rats underwent hysteroovariotomy (OHE) were treated with the present hyaluronan conjugates and then subject to a modified Morrison water maze task to assess the cognitive functions (e.g., learning and memory) of rats.

8 week-old female Sprague-Dawley (SD) rats were used for this study. All animals were caged individually in a temperature (24±1° C.), humidity (60%-65%) and light-controlled room (12/12-hour light-dark-cycle) with food and water ad libitum. All experimental procedures were approved by the Animal Care and Use Committee of National Chung-Hsing University under guidelines of the National Science Council of Taiwan.

For OHE surgery, the rats were deeply anesthetized with 7% chloral hydrate and 2% xylazine (0.45 mL/100 g body weight) and subjected to OHE surgery. Two weeks after the surgery, rats were given test drugs twice weekly for two weeks, and rats were sacrificed four weeks after the surgery.

Five days before the sacrifice, the modified Morrison water maze task started. The maze consisted of a black circular pool of 145 cm in diameter and 22 cm deep. One visual cue (star cardboards) was located at the edge of the pool. A round transparent platform was placed 3 cm below the surface of the water. Animal performance was recorded with a video camera and analyzed with the SMART video tracking system (SMART 3.0V, Panlab, Havard Apparatus, Cambridge, UK).

To assess the escape latency, rats were tested with two trials per day for 3 consecutive days. Rats were randomly placed at different quadrant of the pool facing the wall of the pool. The rats were allowed to remain on the platform for 60 seconds if it escaped within 180 seconds or alternatively placed on the platform for 60 seconds if it failed to locate the underwater platform within 180 seconds. A recovery period of 10 minutes was allowed between the two trials conducted each day. The escape latencies of the two trials each day were averaged for subsequent analyses.

To run the spatial probe test, the platform in the pool was removed and the pool was planned with a virtual target quadrant and a virtual platform according to the previous location of the platform. After the final escape latency task and a one-day break, the rat was placed into the diagonal area of the target quadrant facing the wall of the pool. The rat was allowed to swim for 30 seconds and the swimming path was analyzed.

All experimental data were expressed as mean±SEM. Statistical significance was tested with one-way analysis of variance (ANOVA) followed by the Student-Newman-Keuls (SNK) post hoc test. Differences were considered statistically significant at a p-value <0.05.

In one round of test, OHE rats were treated with 2× E2 (280 ng/kg body weight; n=6), 1× HA-C17-E2 (35 µg/kg body weight; DS: 0.54%; equivalent to 140 ng/kg E2; n=5), or 1.5× HA-C17-E2 (5.25 µg/100 g body weight; DS: 0.54%; equivalent to 210 ng/kg E2; n=5). OHE rats (n=6) and normal rats without OHE surgery (n=4) were used as positive and negative control.

Figure 6A:
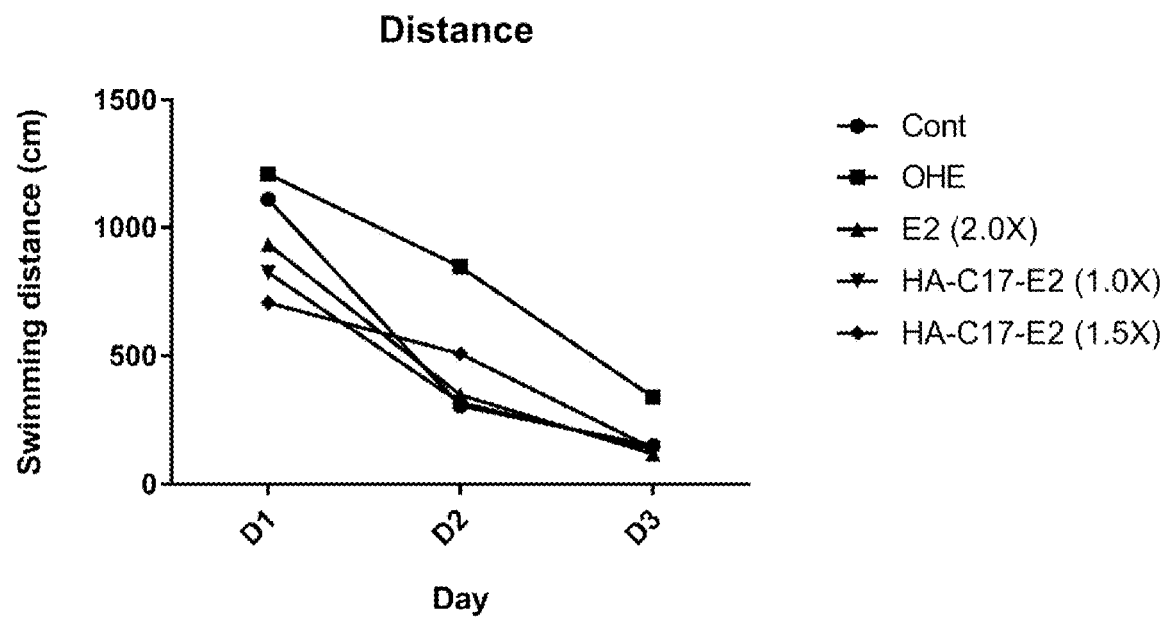
FIG. 6A and FIG. 6B show the in vivo effect of the HA-C17-E2 hyaluronan conjugate on the swimming distance and swimming time in OHE rats, respectively, according to one working example of the present disclosure.
Figure 6B:
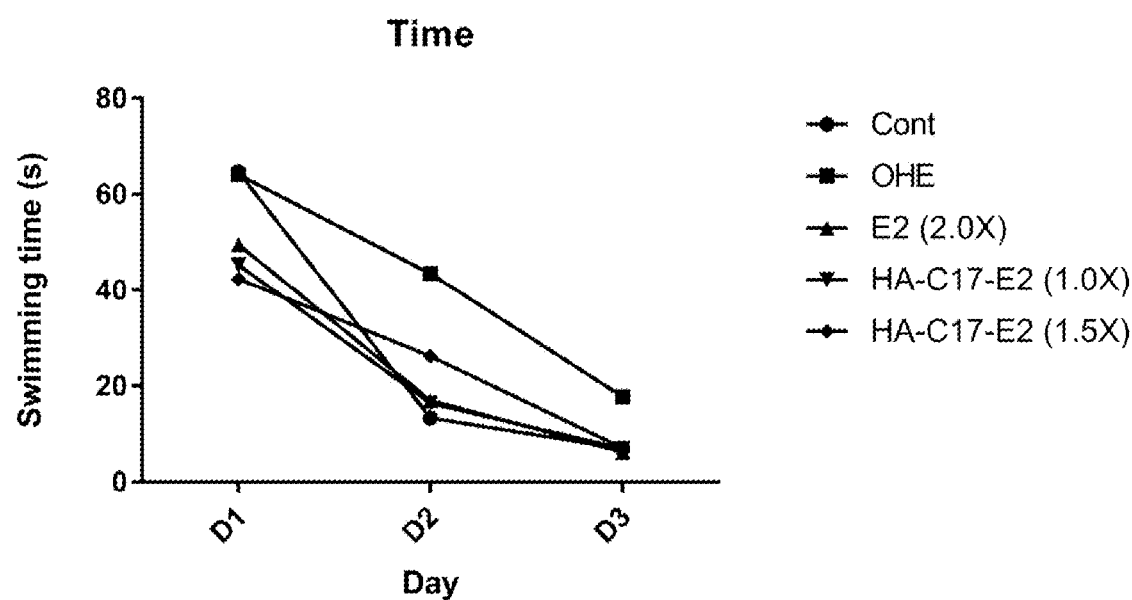

Latency test results summarized in FIG. 6A (swimming distance) and FIG. 6B (swimming time) indicate that the OHE surgery adversely affect the learning function of rats, while the administration of 1× HA-C17-E2, 1.5× HA-C17-E2, and 2× E2 may improve the OHE rats' learning ability with a statistical significance with respect to the OHE group.

Figure 7A:
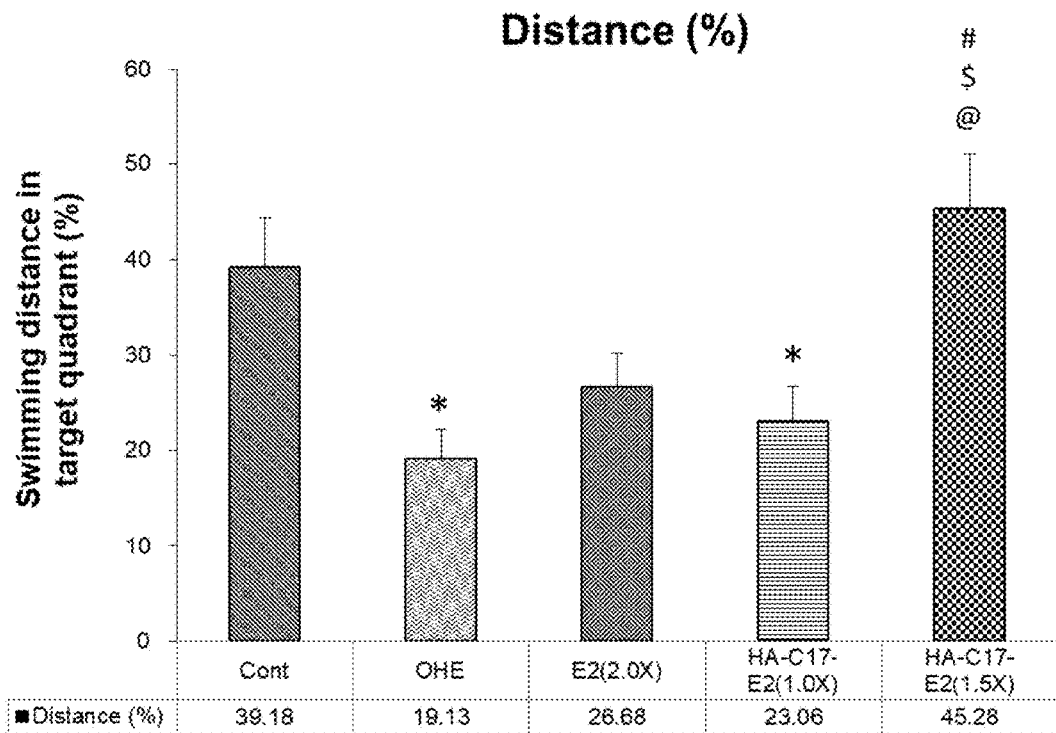
FIG. 7A and FIG. 7B show the in vivo effect of the HA-C17-E2 hyaluronan conjugate on the swimming distance and swimming time in target quadrate in OHE rats, respectively, according to one working example of the present disclosure.
Figure 7B:
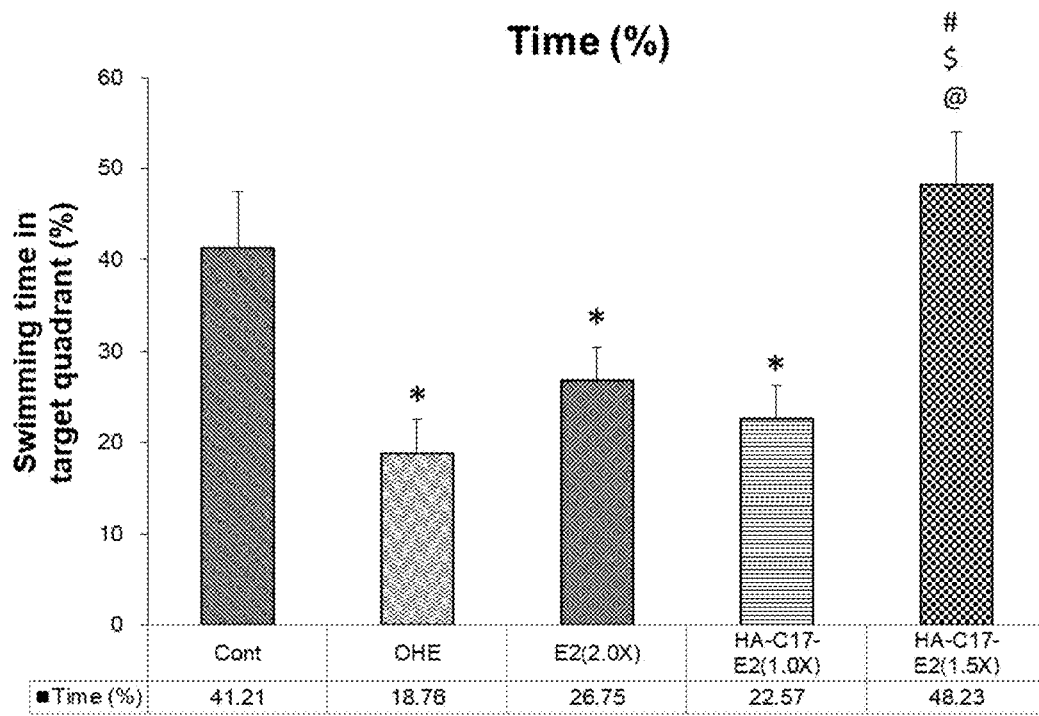

For the spatial probe test, the data provided in FIG. 7A (distance in target quadrate) and FIG. 7B (time in target quadrate) show that the administration of 1.5× HA-C17-E2 significantly improved the rat's memory function with respect to the OHE treated group (#, p<0.05) 1× HA-C17-E2 group (@, p<0.05) and the 2× E2 group ($, p<0.05). Since the preliminary data from this example show that 2× E2 is less effective in promoting the learning and memory function of OHE rats, compared with the 1.5× HA-C17-E2 with only 75% of equivalent E2 with respect to 2× E2, in the subsequent test, the amount of E2 given to OHE rats was further increased.

In another round of test, OHE rats were treated with 2.5× E2 (350 ng/kg body weight; n=16) or 1.5× HA-C17-E2 (52.5 µg/kg body weight; equivalent to 210 ng/kg body weight; n=16). OHE rats (n=8) and normal rats without OHE surgery (n=8) were used as positive and negative control.

Figure 8A:
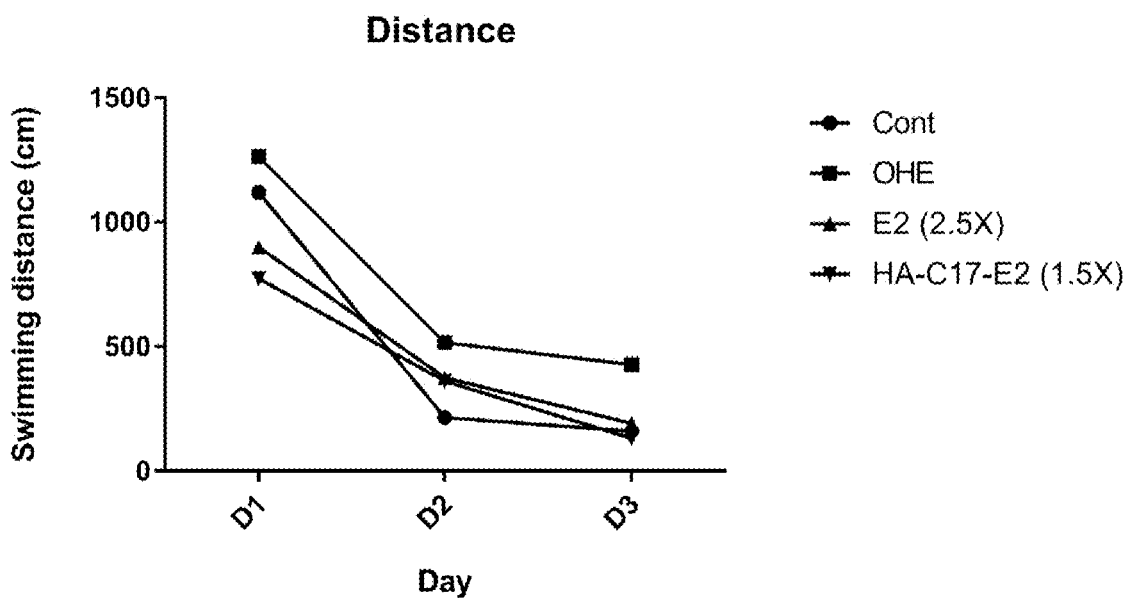
FIG. 8A and FIG. 8B show the in vivo effect of the HA-C17-E2 hyaluronan conjugate on the swimming distance and swimming time in OHE rats, respectively, according to one working example of the present disclosure.
Figure 8B:
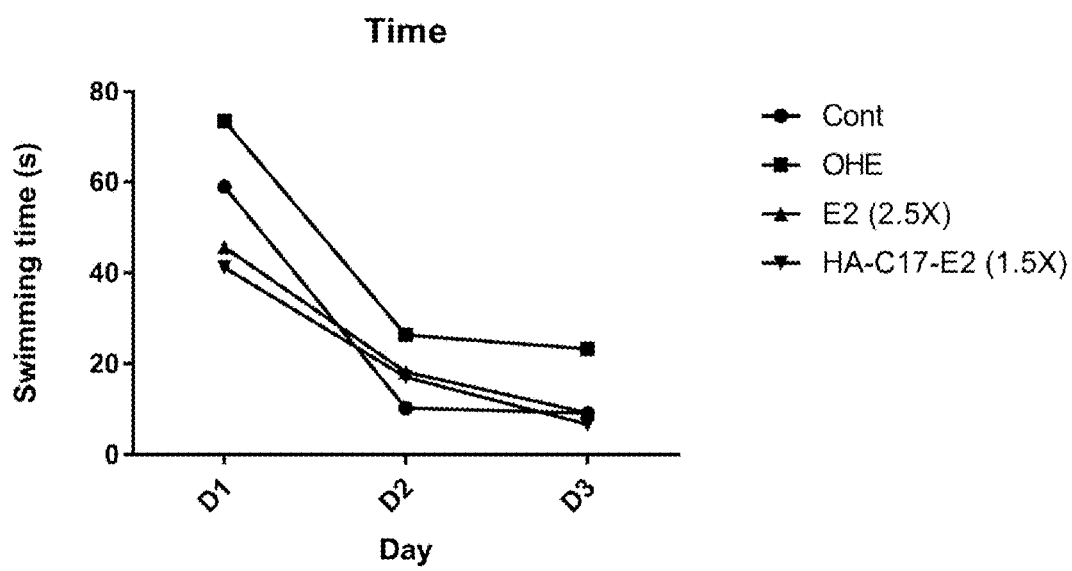

Latency test results summarized in FIG. 8A (swimming distance) and FIG. 8B (swimming time) indicate that the OHE surgery adversely affect the learning function of rats, while the administration of 1.5× HA-C17-E2 and 2.5× E2 may improve the OHE rats' learning ability with a statistical significance with respect to the OHE group on day 3 (#, p<0.05).

Figure 9A:
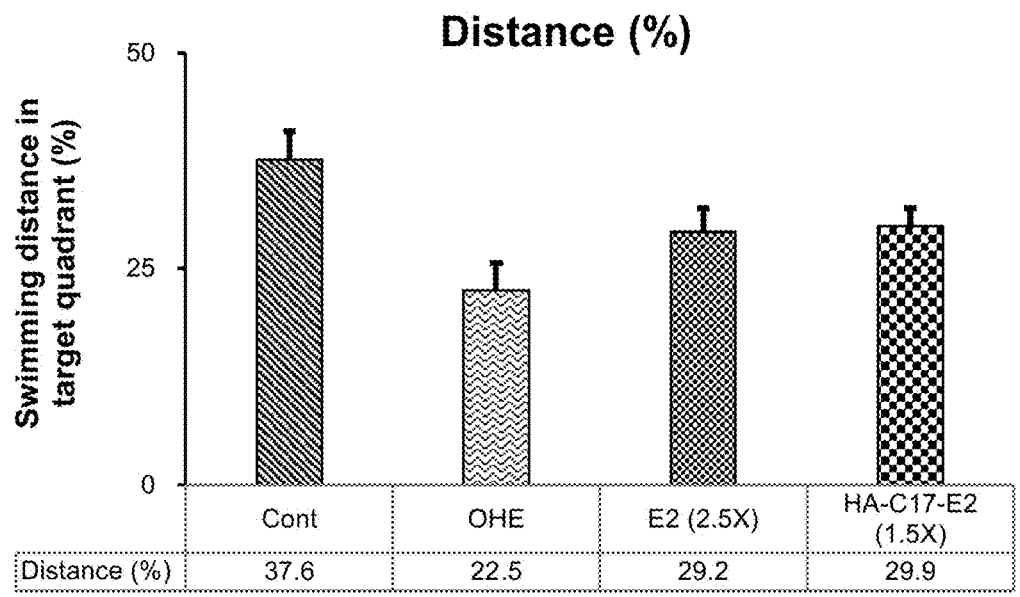
FIG. 9A and FIG. 9B show the in vivo effect of the HA-C17-E2 hyaluronan conjugate on the swimming distance and swimming time in target quadrate in OHE rats, respectively, according to one working example of the present disclosure.
Figure 9B:
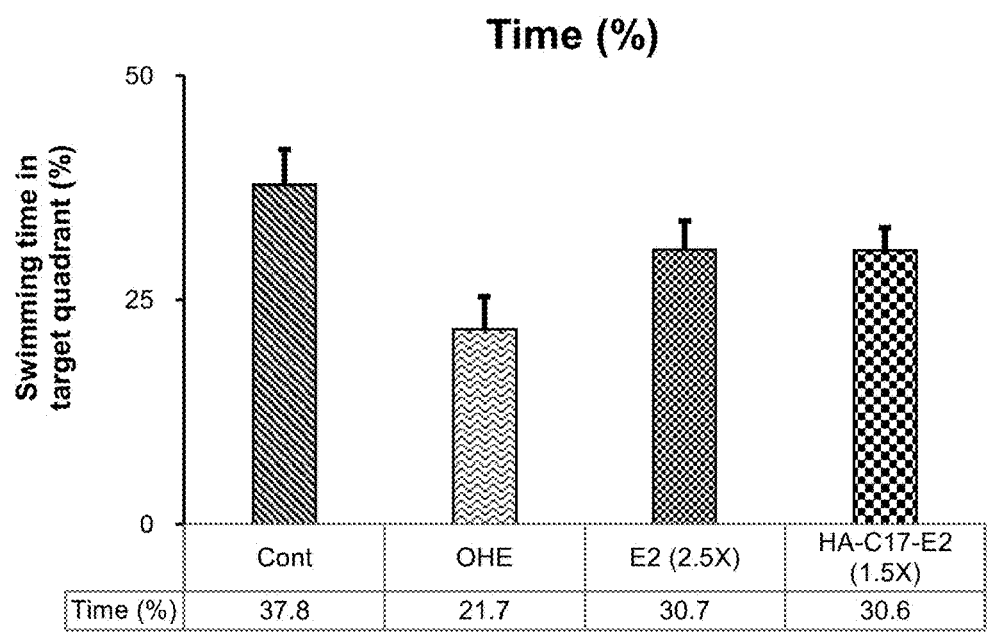

For the spatial probe test, the data provided in FIG. 9A (distance in target quadrate) and FIG. 9B (time in target quadrate) show that the administration of 1.5× HA-C17-E2 and 2.5× E2 significantly improved the rat's memory function with respect to the OHE treated group (#, p<0.05).

It should be noted that in the second round of experiments, the rats treated with 1.5× HA-C17-E2 or 2.5× E2 both show significant improvement in cognitive functions; however, the amount of the equivalent E2 in the 1.5× HA-C17-E2 treatment is only 60% of that in the 2.5× E2 treatment.

Example 6

Effect of Hyaluronan Conjugates on Dendrite Number and Spine Density

The rats were deeply anesthetized with 7% chloral hydrate and 2% xylazine (5 mL/kg body weight) and fixed on the dissection table. Tissue preparation for intracellular dye injection and immunohistochemical staining were performed as follows. Briefly, rats were transcardially perfused with 2% paraformaldehyde in 0.1 M phosphate buffer (PB), pH 7.3, for 30 minutes. Brains were carefully removed and sectioned with vibratome (Technical Products International, St. Louis, Mo.) into two parts: (1) two pieces of 350-µm-thick coronal slices contain hippocampus for intracellular dye injection; (2) 1000-µm-thick coronal slices contained medial septal (MS) nucleus and 2000-µm-thick coronal slices contained hippocampus for immunohistochemical staining. The thick slices for immunohistochemical staining were postfixed in 4% paraformaldehyde in 0.1 M PB for 1 day. The slices for intracellular dye injection were soaked in 10-7 M 4',6-diamidino-2-phenyl-indole (DAPI; Sigma-Aldrich, St. Louis, Mo.) in 0.1 M PB for subsequent processes. The fresh brain tissue containing forebrain basal nucleus, cerebral cortex, and hippocampus were taken by decapitation. The brain tissue was stored in a −70° C. refrigerator for subsequent protein quantification.

Figure 10A:
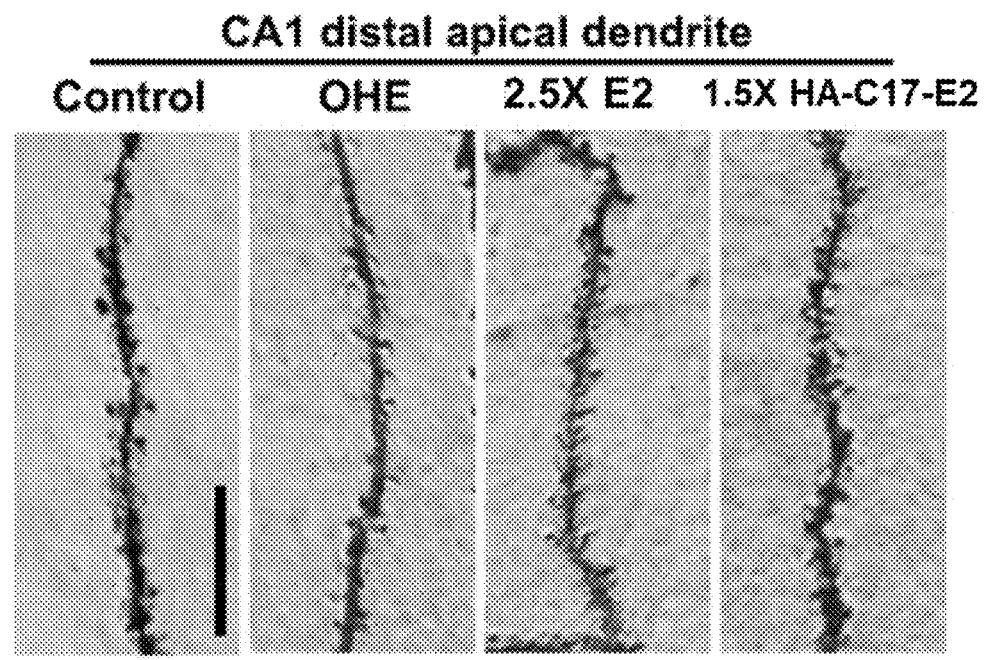
FIG. 10A and FIG. 10B are representative micrographs respectively showing the in vivo effect of the HA-C17-E2 hyaluronan conjugate on the distal apical and distal basal dendrites of pyramidal neurons in hippocampal CA1, according to one working example of the present disclosure.
Figure 10B:
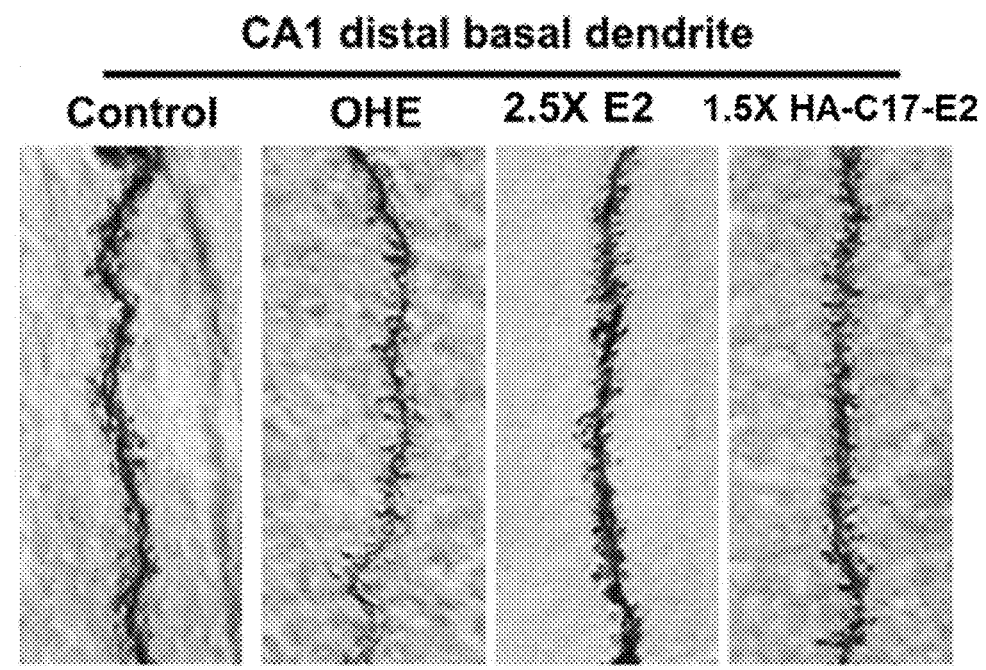

FIG. 10A and FIG. 10B respectively show the photographs of distal apical dendrite and basal apical dendrite in rats. As could be seen in the drawings, OHE rats have less dendrites, compared to control rats that do not undergo OHE surgery. On the other hand, rats treated with 2.5× E2 and 1.5× HA-C17-E2 have more dendrites, compared to OHE treated rats.

Figure 11A:
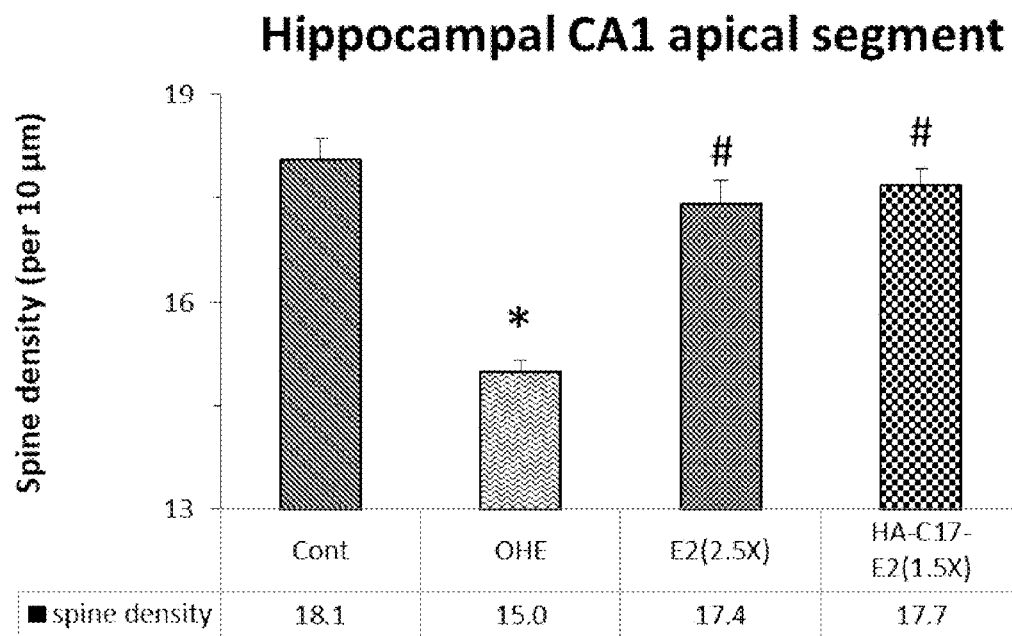
FIG. 11A and FIG. 11B show the in vivo effect of the HA-C17-E2 hyaluronan conjugate on the density of apical and basal dendritic spines of hippocampal CA1 pyramidal neuron in OHE rats, respectively, according to one working example of the present disclosure.
Figure 11B:
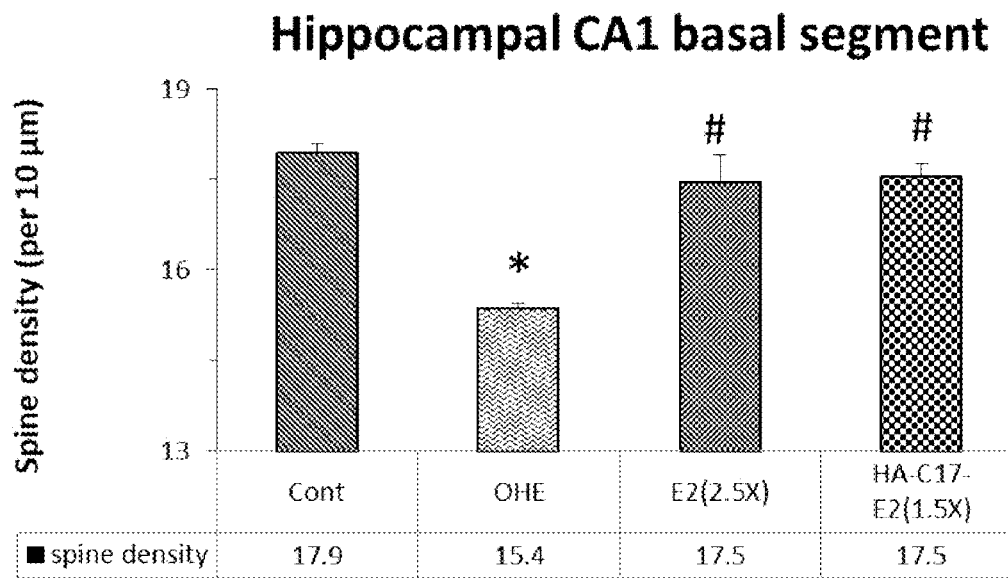

The quantitative results in FIG. 11A (apical segments) and FIG. 11B (basal segments) indicate that OHE surgery is associated with a decrease in spine density, compared to control rats (*, p<0.05). On the other hand, although the administration of 1.5× HA-C17-E2 and 2.5× E2 both result in a significant improvement of the spine density, compared to OHE rats (#, p<0.05), the rats treated with 1.5× HA-C17-E2 have a slightly higher spine density with respect to rats treated with 2.5× E2. It is unexpected to see this result, considering the fact that the amount of estradiol given to the 1.5× HA-C17-E2 treated group is only 60% of that given to 2.5× E2 treated group.

The dorsal hippocampus was randomly chosen three sections in each rat. To determine the density of dendritic spines in hippocampus, distal apical and distal basal dendrites of CA1 pyramidal cell was analyzed. Five independent cells of the hippocampal CA1 region and 3 segments from each dendrite were randomly counted per 10 µm. All data were expressed as mean±SEM. Statistical significance was tested with one-way analysis of variance (ANOVA) followed by the Student-Newman-Keuls (SNK) post hoc test for the spine density. Differences were considered statistically significant at p<0.05.

Example 7

Effect of Hyaluronan Conjugates on Sensorimotor Function

In this example, the pole and beam traversal test (pole test) was carried out to assess the effect of the present hyaluronan conjugate on the sensorimotor function of mice.

8 week-old male C57BL/6 mice (n=4-5 per group) purchased from BioLASCO Taiwan Co., Ltd were used for this study. All animals were caged individually in a temperature (24±1° C.), humidity (60%-65%) and light-controlled room (12/12-hour light-dark-cycle) with food and water ad libitum. All experimental procedures were approved by the Animal Care and Use Committee of National Chung-Hsing University under guidelines of the National Science Council of Taiwan.

Methyl-4-phenyl-1,2,3,6-tetrahydropyridine (MPTP; 20 mg/kg) was intraperitoneally (i.p.) administered to mice four times a day at a 2-hour interval on the 1st and 5th day in the MPTP-induction group. 5× E2 (342 ng/kg) and 2.5× or 5× HA-C17-E2 conjugate (1.96 or 3.92 µg/kg body weight; DS: 13.55%; equivalent to 171 or 342 ng/kg E2) were intravenously (i.v.) administrated to the experimental animal on the 2nd day and 6th day. The Sham group was treated with either intraperitoneal injection of saline or intravenous injection of PBS buffer in the same way.

The mice were subject to a pre-test two days before the MPTP-induction, and on day 2 and day 6, the pole test was carried out 4 hours after the drug administration. Briefly, a tube of 50 cm in length and 1 cm in diameter was used, and a pole was attached to the top of the tube. Animals will often naturally orient themselves downward and descend the length of the pole in order to return to their home cage. The mice returning to their home cage by climbing were given a score of "0". On the other hand, the mice who failed to turn and instead kept their body in a position horizontal to the pole and climbed down often in a corkscrew-like manner were scored "1." Results were analyzed using the Chi-Squared test of independence in IBM SPSS Statistical 20.0 software; significance was set at p<0.05.

Figure 12:
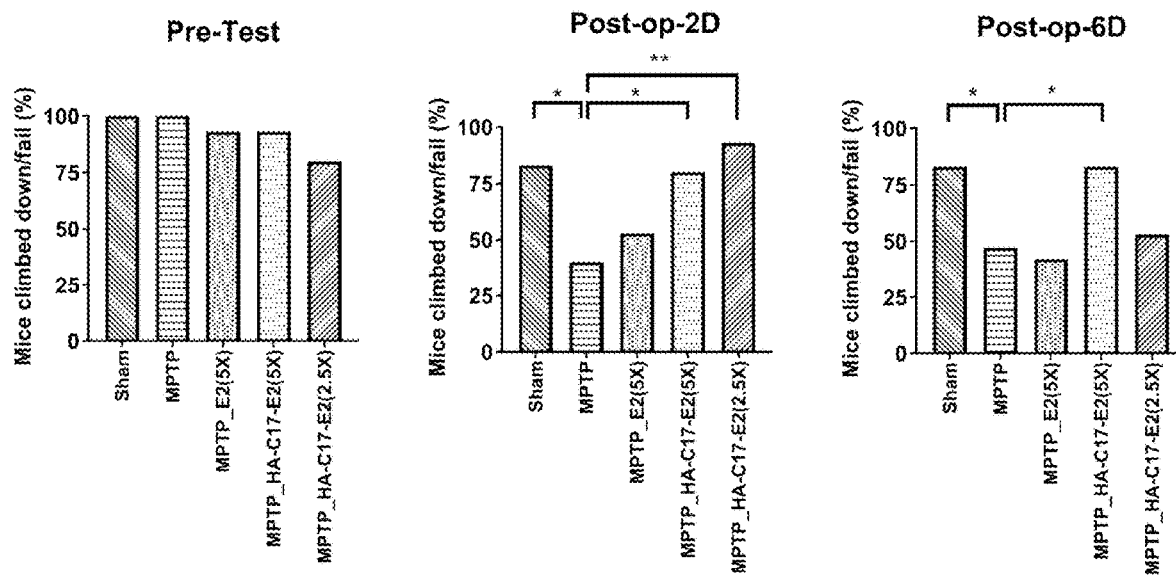
FIG. 12 show the in vivo effect of the HA-C17-E2 hyaluronan conjugate on the learning ability of MPTP-treated mice, according to one working example of the present disclosure.

The results summarized in FIG. 12 indicate that the MPTP induction adversely affect the motor coordination function of mice (*, p<0.05), and the administration of 5× E2 does not effectively improve the motor coordination function of MPTP-treated mice. In contrast, the administration of 2.5× or 5× HA-C17-E2 significantly improve the motor coordination function of MPTP-treated mice (*, p<0.05).

The above examples provide several in vitro and in vivo test results, which establish that the present hyaluronan conjugates are capable of promoting the dendritic spine density, improving cognitive functions (such as learning and memory), and boosting sensorimotor functions. Taken together, these experimental data demonstrate that the present hyaluronan conjugates indeed could prevent the manifestation of neurodegeneration in mice and rats, thus may serve as a prominent candidate for developing a medicament for treating a neurodegenerative disease such as Alzheimer's disease, Parkinson's disease, amyotrophic lateral sclerosis, multiple sclerosis, Huntington's disease, frontotemporal dementia, epilepsy, neuropathic pain, or ataxia.

It will be understood that the above description of embodiments is given by way of example only and that various modifications may be made by those with ordinary skill in the art. The above specification, examples and data provide a complete description of the structure and use of exemplary embodiments of the invention. Although various embodiments of the invention have been described above with a certain degree of particularity, or with reference to one or more individual embodiments, those with ordinary skill in the art could make numerous alterations to the disclosed embodiments without departing from the spirit or scope of this invention.

What is claimed is:

1. A hyaluronan conjugate, comprising:
    a hyaluronic acid (HA) or salt thereof;
    a sex hormone, selected from the group consisting of, estrone, estradiol, estriol, testosterone, and 11-deoxycorticosterone; and
    a linker, covalently coupling the sex hormone with one of the disaccharide units of the HA or salt thereof, wherein the linker is selected from the group consisting of, one or more β-alanine (β-ALA), lipid, dihydrazide-$C_2$-$C_{20}$ dicarboxylic acid, and $C_2$-$C_{20}$ dicarboxylic acids.

2. The hyaluronan conjugate of claim 1, wherein the hyaluronan conjugate has a degree of substitution with the sex hormone of 0.1 to 60%.

3. The hyaluronan conjugate of claim 1, wherein the HA or derivative or salt thereof has a weight-average molecular weight (Mw) of about 5 to 500 kilodaltons (kDa).

4. The hyaluronan conjugate of claim 2, wherein the linker is covalently coupled to the hydroxyl group (—OH) of the sex hormone.

5. The hyaluronan conjugate of claim 1, wherein the dihydrazide-$C_2$-$C_{20}$ dicarboxylic acid is adipic dihydrazide (ADH)-succinate.

6. The hyaluronan conjugate of claim 1, wherein the $C_2$-$C_{20}$ dicarboxylic acids is succinic acid.

7. A pharmaceutical composition for treating a neurodegenerative disease, comprising an effective amount of a hyaluronan conjugate according to claim 1 and a pharmaceutically-acceptable excipient, wherein the neurodegenerative disease is Alzheimer's disease (AD), Parkinson's disease (PD), amyotrophic lateral sclerosis (ALS), multiple sclerosis (MS), Huntington's disease (HD), frontotemporal dementia, epilepsy, neuropathic pain, or ataxia.

* * * * *